United States Patent [19]

Chou et al.

[11] Patent Number: 4,880,838

[45] Date of Patent: * Nov. 14, 1989

[54] PESTICIDAL 1-(4-PHENOXYPHENYL)-5-BENZOYL UREA COMPOUNDS AND PROCESS FOR PREPARATION

[75] Inventors: David T. Chou, Raleigh; Paul A. Cain, Cary, both of N.C.

[73] Assignee: Rhone-Poulenc, Amstelveen, Netherlands

[ * ] Notice: The portion of the term of this patent subsequent to Oct. 10, 2006 has been disclaimed.

[21] Appl. No.: 168,619

[22] Filed: Mar. 7, 1988

Related U.S. Application Data

[63] Continuation of Ser. No. 717,784, Mar. 29, 1985, abandoned, which is a continuation-in-part of Ser. No. 495,331, May 20, 1983, abandoned, which is a continuation-in-part of Ser. No. 393,553, Jun. 30, 1982, abandoned.

[51] Int. Cl.$^4$ ............... C07C 127/22; A01N 47/34
[52] U.S. Cl. ................................. 514/594; 564/44
[58] Field of Search ............ 564/23, 44; 514/584, 514/594

[56] References Cited

U.S. PATENT DOCUMENTS

| | | |
|---|---|---|
| 3,933,908 | 1/1976 | Wellinga et al. ............ 564/44 |
| 3,992,553 | 11/1976 | Sirrenberg et al. .......... 424/304 |
| 4,005,223 | 1/1977 | Sirrenberg et al. .......... 424/322 |
| 4,041,177 | 8/1977 | Sirrenberg et al. .......... 424/322 |
| 4,064,267 | 12/1977 | Sirrenberg et al. .......... 424/304 |
| 4,068,002 | 1/1978 | Sirrenberg et al. .......... 424/322 |
| 4,123,449 | 10/1978 | Sirrenberg et al. .......... 260/453 AR |
| 4,194,005 | 3/1980 | Sirrenberg et al. .......... 424/304 |
| 4,350,706 | 9/1982 | Brouwer et al. ............ 564/44 X |
| 4,355,178 | 10/1982 | Toke et al. ............... 564/44 |
| 4,399,152 | 8/1983 | Brouwer et al. ............ 564/44 X |
| 4,426,385 | 1/1984 | Cain .................... 424/263 |
| 4,508,734 | 4/1985 | Lange et al. ............. 564/44 XR |
| 4,533,676 | 8/1985 | Sirrenberg et al. .......... 564/44 |
| 4,596,890 | 6/1986 | Kisida et al. ............. 564/44 |

FOREIGN PATENT DOCUMENTS

| | | | |
|---|---|---|---|
| 17484 | 10/1980 | European Pat. Off. . | |
| 44410 | 1/1982 | European Pat. Off. ......... | 564/44 |
| 57888 | 8/1982 | European Pat. Off. ......... | 564/44 |
| 74074 | 3/1983 | European Pat. Off. ......... | 564/44 |
| 0098158 | 1/1984 | European Pat. Off. . | |
| 0016475 | 7/1968 | Japan ................. | 71/120 |
| 0038357 | 3/1980 | Japan ................. | 564/44 |
| 0025144 | 3/1981 | Japan ................. | 564/44 |
| 0092857 | 7/1981 | Japan ................. | 564/44 |
| 0002258 | 1/1982 | Japan ................. | 564/44 |
| 0002259 | 1/1982 | Japan ................. | 564/44 |
| 2062634 | 5/1981 | United Kingdom ......... | 564/44 |
| 2083360 | 3/1982 | United Kingdom . | |

OTHER PUBLICATIONS

Chemical Abstracts, Vol. 95, No. 23, Page 645, Abstract No. 203586e, Dec. 7, 1981.

Primary Examiner—Charles F. Warren
Assistant Examiner—Carolyn Gleason
Attorney, Agent, or Firm—Morgan & Finnegan

[57] ABSTRACT

Novel 1-(4-phenoxyphenyl)-3-benzoyl urea compounds are provided together with methods for their preparation and the use of said compounds as the active toxicant in pesticidal compositions.

64 Claims, No Drawings

PESTICIDAL 1-(4-PHENOXYPHENYL)-5-BENZOYL UREA COMPOUNDS AND PROCESS FOR PREPARATION

This is a continuation of co-pending application Ser. No. 717,784, filed Mar. 29, 1985.

This application is a continuation-in-part of U.S. patent application Ser. No. 495,331, filed May 20, 1983, which is a continuation-in-part of U.S. patent application Ser. No. 393,553, filed June 30, 1982.

BRIEF SUMMARY OF THE INVENTION

1. Technical Field

This invention relates to novel 1-(4-phenoxyphenyl)-3-benzoyl urea compounds which are useful as the active toxicant in pesticidal compositions. This invention also relates to a method for the preparation of the novel 1-(4-phenoxyphenyl)-3-benzoyl urea compounds. This invention further relates to pesticidal compositions and to a method for their use.

2. Background of the Invention

In recent years a variety of benzoyl urea compounds have been reported in the literature as having pesticidal activity. For example, benzoylureido-diphenyl ethers and their use as insecticides have been disclosed in U.S. Pat. No. 4,005,223 issued Jan. 25, 1977, U.S. Pat. No. 4,041,177 issued Aug. 9, 1977, and U.S. Pat. No. 4,068,002 issued Jan. 10, 1978. Also, N-benzoyl-N'-phenoxyphenyl urea compounds and their use as insecticides have been disclosed in U.S. Pat. No. 4,399,152 issued Aug. 16, 1983, Japanese Patent Application No. 55 038 357 published Mar. 17, 1980, Japanese Patent Application No. 5 6092 857 published July 27, 1981, and Japanese Patent Application No. 57 002 258 published Jan. 7, 1982. N-benzoyl-N'-phenoxypyridyl urea compounds have been disclosed in European Patent No. 0069288 issued Jan. 12, 1983.

Accordingly, one or more of the following objects will be achieved by the practice of this invention. It is an object of this invention to provide novel 1-(4-phenoxyphenyl)-3-benzoyl urea compounds. Another object of this invention is to provide certain 1-(4-phenoxyphenyl)-3-benzoyl urea compounds which exhibit excellent insecticidal activity. A still further object of this invention is to provide novel benzoyl urea compounds, such as 1-[3-chloro-4-(2,4-dichlorophenoxy)-2,5-dimethylphenyl]-3-(2,6-difluorobenzoyl) urea, 1-[3-chloro-4-(2-bromo-4-chlorophenoxy)-2,5-dimethylphenyl]-3-(2,6-difluorobenzoyl) urea, 1-[3-chloro-4-(2-bromo-4-chlorophenoxy)-2,5-dimethylphenyl]-3-(2-fluorobenzoyl) urea, etc. Another object is to provide processes for the preparation of the novel benzoyl urea compounds. A further object is to provide novel pesticidal compositions containing the novel benzoyl urea compounds as the active toxicant. Another object of the invention is to provide a method for controlling pests by the application of the novel pesticidal compositions. These and other objects will readily become apparent to those skilled in the art in the light of the teachings herein set forth.

DISCLOSURE OF THE INVENTION

In its broad aspect the invention relates to novel 1-(4-phenoxyphenyl)-3-benzoyl urea compounds, pesticidal compositions containing the same, and processes for their preparation and use. The benzoyl urea compounds of this invention can be represented by the following formula:

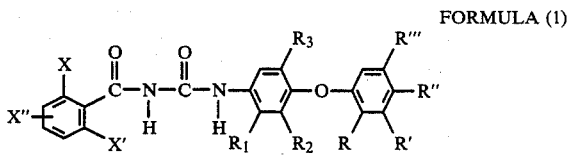

FORMULA (1)

wherein:
X represents halogen;
X' represents hydrogen or halogen;
X" represents fluorine or hydrogen with the proviso that when X' is halogen then X" is hydrogen;
$R_1$, $R_2$ and $R_3$ are independently methyl, chlorine or bromine;
R represents methyl, chlorine, fluorine or bromine; and
R', R" and R"' are independently hydrogen, methyl, chlorine, fluorine or bromine provided that at least one of R', R" and R"' is other than hydrogen.

DETAILED DESCRIPTION

As indicated above, the invention relates to novel 1-(4-phenoxyphenyl)-3-benzoyl urea compounds, pesticidal compositions containing the same, and processes for their preparation and use.

Preferred benzoyl urea compounds within the broad generic Formula (1) are those having the formulas:

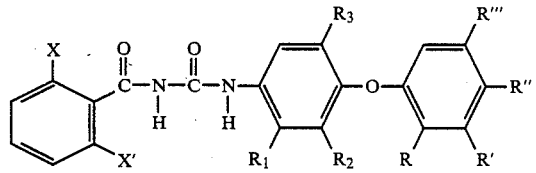

wherein X, X', $R_1$, $R_2$, $R_3$, R, R', R" and R"' are as indicated above.

Particularly preferred benzoyl urea compounds are those of the formulas:

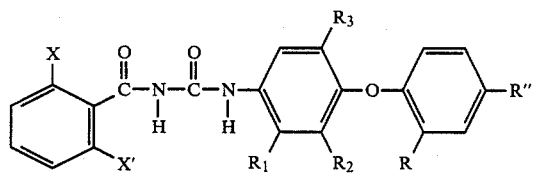

wherein X, X', $R_1$, $R_2$, $R_3$, R and R" are as indicated above; and

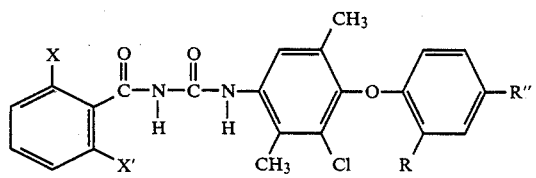

wherein X, X', R, and R" are as indicated above.

The following benzoyl urea compounds listed in Tables A through G are illustrative of those encompassed by the above formulas and which can be prepared by the practice of this invention:

TABLE A

Representative 1-(4-Phenoxyphenyl)-3-Benzoyl Urea Compounds

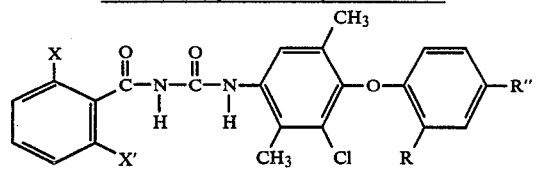

| X | X' | R | R'' |
|---|----|---|-----|
| F | F | Cl | Cl |
| Cl | H | Cl | Cl |
| F | Cl | Cl | Cl |
| Cl | Cl | Cl | Cl |
| Br | F | Cl | Cl |
| Cl | Br | Cl | Cl |
| H | F | Cl | Cl |
| Br | H | Cl | Cl |
| F | F | Br | Cl |
| F | H | Br | Cl |
| H | Cl | Br | Cl |
| Cl | Cl | Br | Cl |
| Cl | F | Br | Cl |
| F | F | Br | Br |
| H | F | Br | Br |
| Cl | Cl | Br | Br |
| Cl | Br | Br | Br |
| Cl | F | Br | Br |
| F | F | CH$_3$ | CH$_3$ |
| Cl | H | CH$_3$ | CH$_3$ |
| H | F | CH$_3$ | CH$_3$ |
| Cl | F | CH$_3$ | CH$_3$ |
| Cl | Cl | CH$_3$ | CH$_3$ |
| F | F | Br | CH$_3$ |
| F | F | CH$_3$ | Br |
| F | F | Cl | CH$_3$ |
| F | F | CH$_3$ | Cl |
| F | F | F | Cl |
| F | F | F | Cl |
| H | F | F | F |
| Cl | H | F | F |
| F | F | F | F |
| Cl | H | Cl | F |
| F | F | Cl | F |
| H | Cl | F | Br |
| F | F | F | Br |
| F | F | Br | F |

TABLE B

Representative 1-(4-Phenoxyphenyl)-3-Benzoyl Urea Compounds

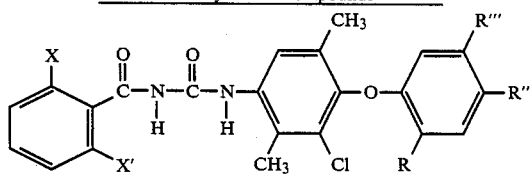

| X | X' | R | R'' | R''' |
|---|----|---|-----|------|
| F | F | Cl | H | Cl |
| Cl | H | Cl | H | Cl |
| F | H | Cl | H | Cl |
| H | F | Cl | H | Cl |
| H | Cl | Cl | Cl | Cl |
| F | F | Cl | Cl | Cl |
| H | Cl | Cl | Br | Cl |
| F | H | Cl | Br | Cl |
| F | F | Cl | Br | Cl |
| F | F | Br | Cl | Cl |
| Cl | H | Br | Cl | Cl |
| Cl | F | Br | Cl | Cl |
| F | H | Br | Cl | Cl |
| Cl | F | Br | CH$_3$ | Cl |
| F | F | Br | CH$_3$ | Cl |
| Cl | H | Br | CH$_3$ | Cl |

TABLE B-continued

Representative 1-(4-Phenoxyphenyl)-3-Benzoyl Urea Compounds

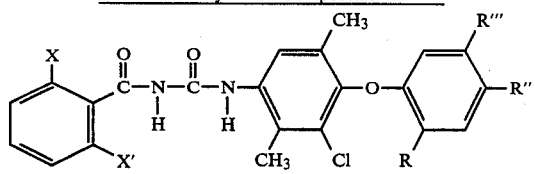

| X | X' | R | R'' | R''' |
|---|----|---|-----|------|
| F | F | CH$_3$ | CH$_3$ | CH$_3$ |
| Cl | F | CH$_3$ | CH$_3$ | CH$_3$ |
| F | H | CH$_3$ | CH$_3$ | CH$_3$ |
| F | F | CH$_3$ | Cl | CH$_3$ |
| H | Cl | CH$_3$ | Cl | CH$_3$ |
| F | H | CH$_3$ | Cl | CH$_3$ |
| F | F | CH$_3$ | Cl | Cl |
| H | Cl | CH$_3$ | Cl | Cl |
| F | H | CH$_3$ | Cl | Cl |
| F | F | CH$_3$ | Br | Cl |
| Cl | F | CH$_3$ | Br | Cl |
| Cl | Cl | CH$_3$ | Br | Cl |
| Cl | H | Br | Br | CH$_3$ |
| F | H | Br | Br | CH$_3$ |
| F | F | Br | Br | CH$_3$ |
| F | H | Br | Cl | Br |
| Cl | H | Br | Cl | Br |
| F | F | Br | Cl | Br |
| F | F | CH$_3$ | F | CH$_3$ |
| F | F | CH$_3$ | CH$_3$ | F |
| F | F | Cl | F | Cl |
| F | F | CH$_3$ | H | CH$_3$ |
| F | Cl | CH$_3$ | H | CH$_3$ |
| F | H | CH$_3$ | H | CH$_3$ |
| Cl | H | CH$_3$ | CH$_3$ | CH$_3$ |

TABLE C

Representative 1-(4-Phenoxyphenyl)-3-Benzoyl Urea Compounds

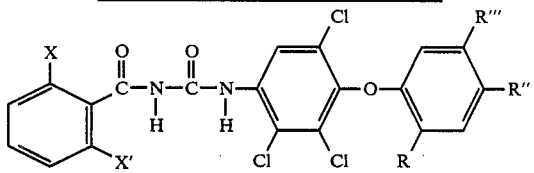

| X | X' | R | R'' | R''' |
|---|----|---|-----|------|
| F | F | Cl | Cl | H |
| H | Cl | Cl | Cl | H |
| F | H | Cl | Cl | H |
| Cl | F | Cl | Cl | H |
| Cl | Cl | Cl | Cl | H |
| F | F | Br | Cl | H |
| H | Cl | Br | Cl | H |
| Cl | F | Br | Cl | H |
| F | H | Br | Cl | H |
| Cl | Cl | Br | Cl | H |
| F | F | Br | Br | H |
| Cl | H | Br | Br | H |
| H | F | Br | Br | H |
| F | H | Cl | H | Cl |
| F | F | Cl | H | Cl |
| Cl | F | Cl | H | Cl |
| F | F | Br | H | Cl |
| F | H | Br | H | Cl |
| Cl | H | Br | H | Cl |
| F | F | Cl | Cl | Cl |
| Cl | F | Cl | Cl | Cl |
| F | H | Cl | Cl | Cl |
| F | F | CH$_3$ | Cl | Cl |
| Cl | H | CH$_3$ | Cl | CH$_3$ |
| F | H | CH$_3$ | Cl | CH$_3$ |
| F | F | CH$_3$ | CH$_3$ | CH$_3$ |
| H | Cl | CH$_3$ | CH$_3$ | CH$_3$ |
| F | H | CH$_3$ | CH$_3$ | CH$_3$ |

TABLE C-continued

Representative 1-(4-Phenoxyphenyl)-3-Benzoyl Urea Compounds

Structure: benzoyl urea with X, X' on left ring; Cl, Cl, Cl on middle ring; R, R'', R''' on right ring

| X | X' | R | R'' | R''' |
|---|----|---|-----|------|
| F | F | CH$_3$ | Cl | Cl |
| H | F | CH$_3$ | Cl | Cl |
| Cl | H | CH$_3$ | Cl | Cl |
| F | F | CH$_3$ | CH$_3$ | H |
| Cl | H | CH$_3$ | CH$_3$ | H |
| F | F | CH$_3$ | H | CH$_3$ |
| Cl | H | CH$_3$ | H | CH$_3$ |

TABLE D

Representative 1-(4-Phenoxyphenyl)-3-Benzoyl Urea Compounds

Structure with CH$_3$, Cl, CH$_3$ on middle ring; R, R'', R''' on right ring

| X | X' | R | R'' | R''' |
|---|----|---|-----|------|
| F | F | Cl | Cl | H |
| H | F | Cl | Cl | H |
| Cl | H | Cl | Cl | H |
| Cl | F | Cl | Cl | H |
| Cl | Cl | Cl | Cl | H |
| F | F | Br | Cl | H |
| F | H | Br | Cl | H |
| F | Cl | Br | Cl | H |
| Cl | Cl | Br | Cl | H |
| F | Cl | Br | Cl | H |
| F | F | Br | Br | H |
| H | F | Br | Br | H |
| Cl | H | Br | Br | H |
| F | F | Cl | H | Cl |
| F | Cl | Cl | H | Cl |
| Cl | H | Cl | H | Cl |
| F | F | CH$_3$ | Cl | CH$_3$ |
| F | H | CH$_3$ | Cl | CH$_3$ |
| H | Cl | CH$_3$ | Cl | CH$_3$ |
| F | F | CH$_3$ | CH$_3$ | CH$_3$ |
| Cl | H | CH$_3$ | CH$_3$ | CH$_3$ |
| F | H | CH$_3$ | CH$_3$ | CH$_3$ |
| F | F | CH$_3$ | Br | CH$_3$ |
| Cl | H | CH$_3$ | Br | CH$_3$ |
| F | F | Br | Br | Br |
| Cl | H | Br | Br | Br |
| H | Cl | CH$_3$ | Cl | Cl |
| F | F | CH$_3$ | Cl | Cl |
| F | F | CH$_3$ | H | CH$_3$ |
| H | Cl | CH$_3$ | H | CH$_3$ |
| H | Cl | CH$_3$ | CH$_3$ | H |
| F | F | CH$_3$ | CH$_3$ | H |

TABLE E

Representative 1-(4-Phenoxyphenyl)-3-Benzoyl Urea Compounds

Structure with CH$_3$, CH$_3$, CH$_3$ on middle ring; R, R'', R''' on right ring

| X | X' | R | R'' | R''' |
|---|----|---|-----|------|
| F | F | Cl | Cl | H |
| Cl | F | Cl | Cl | H |
| H | F | Cl | Cl | H |
| Cl | H | Cl | Cl | H |
| Cl | Cl | Cl | Cl | H |
| F | F | Br | Cl | H |
| F | Cl | Br | Cl | H |
| F | H | Br | Cl | H |
| Cl | H | Br | Cl | H |
| Cl | Cl | Br | Cl | H |
| F | F | Br | Br | H |
| Cl | F | Br | Br | H |
| Cl | H | Br | Br | H |
| H | F | Br | Br | H |
| F | F | CH$_3$ | CH$_3$ | H |
| Cl | H | CH$_3$ | CH$_3$ | H |
| Cl | F | Cl | H | Cl |
| F | F | Cl | H | Cl |
| Cl | H | Cl | H | Cl |
| Cl | H | CH$_3$ | H | CH$_3$ |
| F | F | CH$_3$ | H | CH$_3$ |
| H | F | CH$_3$ | H | CH$_3$ |
| F | F | Cl | Cl | Cl |
| H | F | Cl | Cl | Cl |
| Cl | H | Cl | Cl | Cl |
| F | F | CH$_3$ | CH$_3$ | CH$_3$ |
| H | F | CH$_3$ | CH$_3$ | CH$_3$ |
| H | Cl | CH$_3$ | CH$_3$ | CH$_3$ |
| F | H | CH$_3$ | Cl | CH$_3$ |
| Cl | H | CH$_3$ | Cl | CH$_3$ |
| F | F | CH$_3$ | Cl | CH$_3$ |

TABLE F

Representative 1-(4-Phenoxyphenyl)-3-Benzoyl Urea Compounds

Structure with X, X', X'' on left ring; R$_1$, R$_2$, R$_3$ on middle ring; Br, CH$_3$, CH$_3$ on right ring

| X | X' | X'' | R$_1$ | R$_2$ | R$_3$ |
|---|----|-----|-------|-------|-------|
| Cl | H | H | CH$_3$ | Cl | CH$_3$ |
| F | H | H | CH$_3$ | Cl | CH$_3$ |
| F | F | H | CH$_3$ | Cl | CH$_3$ |
| Cl | F | H | CH$_3$ | Cl | CH$_3$ |
| Cl | H | 4-F | CH$_3$ | Cl | CH$_3$ |
| Cl | H | 5-F | CH$_3$ | Cl | CH$_3$ |
| F | F | H | CH$_3$ | CH$_3$ | Cl |
| F | H | H | CH$_3$ | CH$_3$ | Cl |
| Cl | F | H | CH$_3$ | CH$_3$ | Cl |
| Cl | H | H | CH$_3$ | CH$_3$ | Cl |
| Cl | H | 4-F | CH$_3$ | CH$_3$ | Cl |
| Cl | H | 5-F | CH$_3$ | CH$_3$ | CH$_3$ |
| F | F | H | CH$_3$ | CH$_3$ | CH$_3$ |
| Cl | H | H | CH$_3$ | CH$_3$ | CH$_3$ |
| Cl | H | 4-F | CH$_3$ | CH$_3$ | CH$_3$ |
| Cl | H | 5-F | CH$_3$ | CH$_3$ | CH$_3$ |
| Cl | H | H | Cl | Cl | Cl |
| F | F | H | Cl | Cl | Cl |
| Cl | H | 4-F | Cl | Cl | Cl |
| Cl | H | 5-F | Cl | Cl | Cl |
| Cl | F | H | Cl | Cl | Cl |
| F | H | H | Cl | CH$_3$ | Cl |
| F | H | H | Cl | CH$_3$ | Cl |

TABLE F-continued
Representative 1-(4-Phenoxyphenyl)-3-Benzoyl Urea Compounds

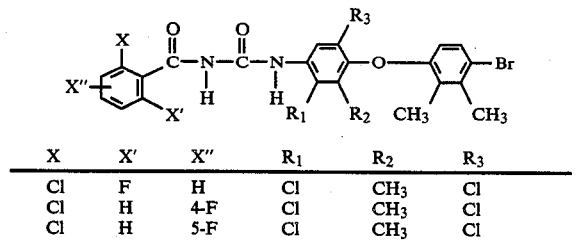

| X | X' | X" | $R_1$ | $R_2$ | $R_3$ |
|---|---|---|---|---|---|
| Cl | F | H | Cl | $CH_3$ | Cl |
| Cl | H | 4-F | Cl | $CH_3$ | Cl |
| Cl | H | 5-F | Cl | $CH_3$ | Cl |

TABLE G
Representative 1-(4-Phenoxyphenyl)-3-Benzoyl Urea Compounds

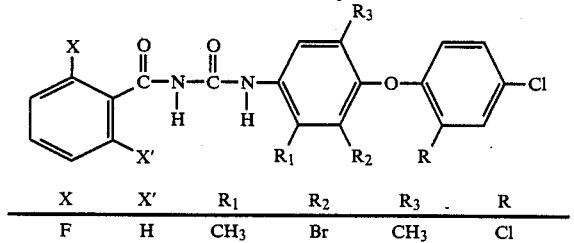

| X | X' | $R_1$ | $R_2$ | $R_3$ | R |
|---|---|---|---|---|---|
| F | H | $CH_3$ | Br | $CH_3$ | Cl |
| Cl | H | $CH_3$ | Br | $CH_3$ | Cl |
| F | F | $CH_3$ | Br | $CH_3$ | Cl |
| F | F | $CH_3$ | Br | $CH_3$ | Br |
| H | Cl | $CH_3$ | Br | $CH_3$ | Br |
| F | H | $CH_3$ | Br | $CH_3$ | Br |
| F | F | Br | Br | Br | Cl |
| Cl | H | Br | Br | Br | Cl |
| F | F | Br | Br | Br | Br |
| Cl | H | Br | Br | Br | Br |
| F | F | Br | $CH_3$ | $CH_3$ | Cl |
| H | Cl | Br | $CH_3$ | $CH_3$ | Cl |
| H | Cl | Br | $CH_3$ | $CH_3$ | Br |
| F | F | Br | $CH_3$ | $CH_3$ | Br |
| F | F | Br | Cl | Cl | Cl |
| H | Cl | Br | Cl | Cl | Cl |
| F | F | Br | Cl | Cl | Br |
| H | Cl | Br | Cl | Cl | Br |
| Cl | H | Br | $CH_3$ | Br | Cl |
| F | F | Br | $CH_3$ | Br | Cl |
| Cl | H | Br | $CH_3$ | Br | Br |
| Br | Br | Br | $CH_3$ | Br | Br |
| H | F | Cl | $CH_3$ | Cl | Cl |
| Cl | H | Cl | $CH_3$ | Cl | Cl |
| F | F | Cl | $CH_3$ | Cl | Cl |
| F | H | Cl | $CH_3$ | Cl | Br |
| Cl | H | Cl | $CH_3$ | Cl | Br |
| F | F | Cl | $CH_3$ | Cl | Br |
| F | F | Cl | Cl | $CH_3$ | Cl |
| Cl | H | Cl | Cl | $CH_3$ | Cl |
| H | F | Cl | Cl | $CH_3$ | Cl |
| F | H | Cl | Cl | $CH_3$ | Br |
| F | F | Cl | Cl | $CH_3$ | Br |
| Cl | H | Cl | Cl | $CH_3$ | Br |
| F | F | $CH_3$ | Cl | Cl | Cl |
| F | H | $CH_3$ | Cl | Cl | Cl |
| H | Cl | $CH_3$ | Cl | Cl | Cl |
| H | F | $CH_3$ | Cl | Cl | Br |
| H | Cl | $CH_3$ | Cl | Cl | Br |
| F | F | $CH_3$ | Cl | Cl | Br |
| F | F | Cl | $CH_3$ | Br | Cl |
| Cl | H | Cl | $CH_3$ | Br | Cl |
| H | F | $CH_3$ | Cl | Br | Cl |
| F | F | $CH_3$ | Cl | Br | Cl |
| Cl | H | $CH_3$ | Cl | Br | Cl. |
| F | F | Cl | $CH_3$ | Br | Br |
| H | Cl | Cl | $CH_3$ | Br | Br |

The novel benzoyl urea compounds of this invention can be conveniently prepared by one or more methods. For example, the compounds of this invention may be prepared by reacting a substituted phenoxyaniline 2 with a benzoyl isocyanate 3 according to Scheme I as follows:

Scheme I

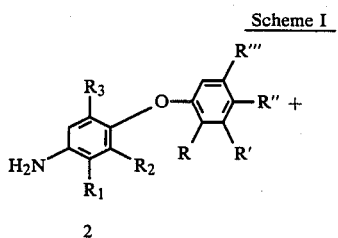

2

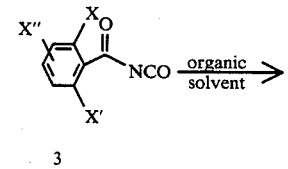

3

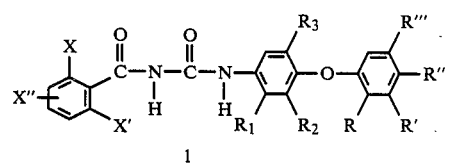

1 wherein X, X', X", $R_1$, $R_2$, $R_3$, R, R', R" and R''' have the meaning given to Formula (1).

Alternatively, the novel compounds may be prepared by the reaction of an phenoxyphenylisocyanate 4 with a benzamide 5 according to Scheme II as follows:

Scheme II

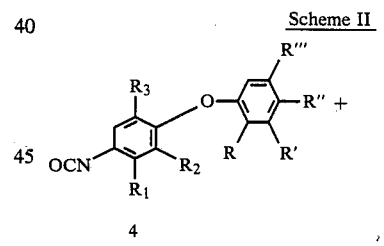

4

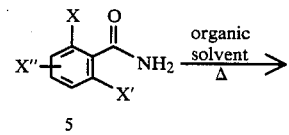

5

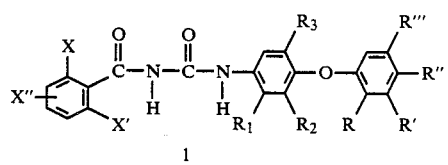

1 wherein X, X', X", $R_1$, $R_2$, $R_3$, R, R', R" and R''' have the meaning given to Formula (1).

The subject compounds may also be prepared by the reaction of a benzoyl chloride 6 with a substituted urea 7 according to Scheme III as follows:

Scheme III

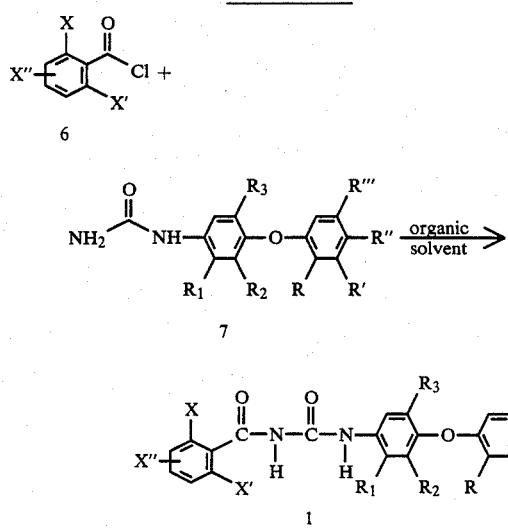

wherein X, X', X", $R_1$, $R_2$, $R_3$, R, R', R" and R'" have the meaning given to Formula (1).

In general, the reactions illustrated in Schemes I, II and III can be carried out in organic solvents such as aromatic hydrocarbons, halogenated hydrocarbons, ethers, and the like. Solvents like toluene, 1,2-dichloroethane, dichloromethane and p-dioxane are preferred. These reactions proceed at temperatures ranging from ambient temperature to 150° C.

The intermediates shown in Schemes I, II and III can be prepared according to generally accepted procedures. Thus, the substituted benzoyl isocyanate 3 can be prepared from the corresponding benzamide 5 following the general procedure of Speziale et. al., *J. Org. Chem.* 27, 3742 (1962) as follows:

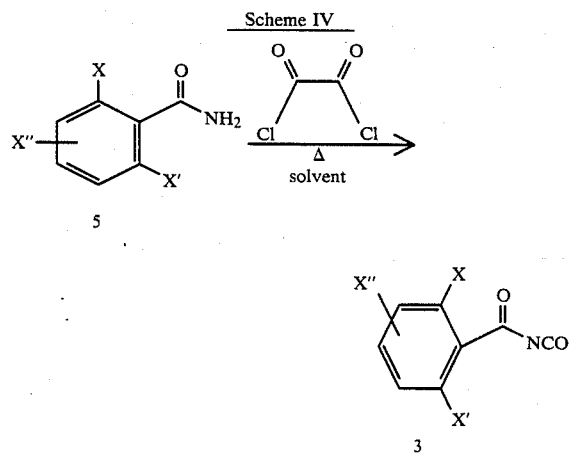

wherein X, X' and X" have the meaning given in Formula (1).

The substituted phenoxyanilines 2 for which $R_1$ is not chlorine or bromine may be prepared according to Scheme V involving the reaction of a substituted phenol 9 with a chloronitrobenzene 8 as follows:

Scheme V

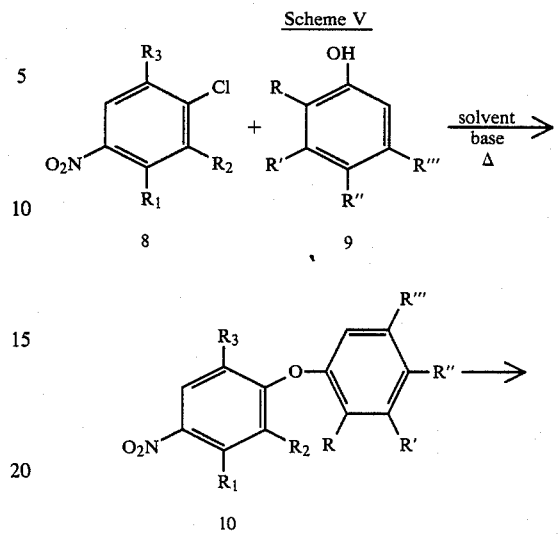

wherein $R_1$, $R_2$, $R_3$, R, R', R" and R'" have the meaning given in Formula (1) with the proviso that $R_1$ is not chlorine or bromine. The reaction of a substituted phenol 9 with a chloronitrobenzene 8 to give the nitro ether 10 proceeds in the presence of a base in an inert solvent at elevated temperature. Bases suitable for this reaction are potassium carbonate, sodium hydride, potassium hydroxide, and sodium hydroxide. Suitable solvents are toluene, dimethylformamide, and dimethylsulfoxide. The above transformation can be carried out in a diphasic reaction medium in the presence of a phase-transfer catalyst.

The reduction of nitro ether 10 to phenoxyaniline 2 can be achieved by hydrogenation using a catalytic amount of platinum or palladium on carbon or a Raney Nickel catalyst under an atmosphere of hydrogen at a pressure ranging from 40–200 psi at ambient temperature. Suitable solvents for hydrogenation include aromatic hydrocarbons or alcohols. The reduction can also be achieved by a chemical method using hydrazine and a metal catalyst as disclosed in *Chem. Rev.*, Vol. 65, pp. 51–68 (1965).

Isocyanate 4 can be obtained by reacting the substituted aniline 2 with phosgene. Urea 7 may be obtained via the reaction of isocyanate 4 with ammonium hydroxide or gaseous ammonia. These reactions are illustrated in Scheme VI below as follows:

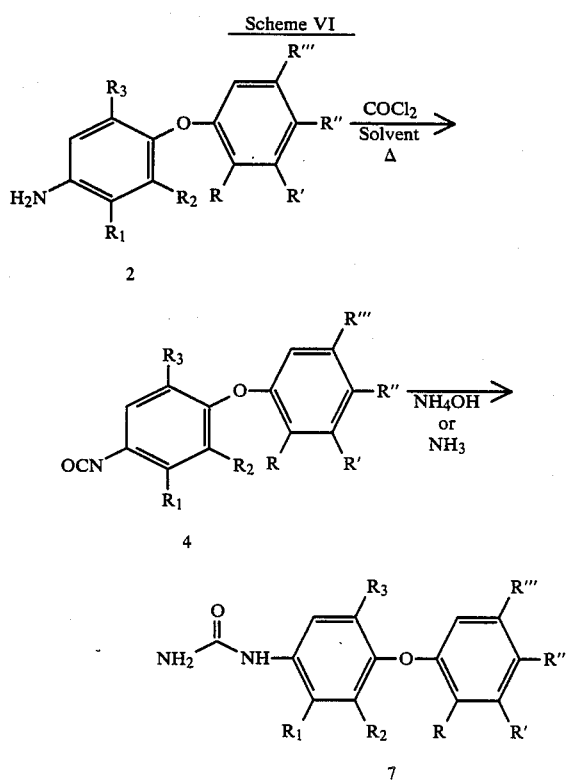

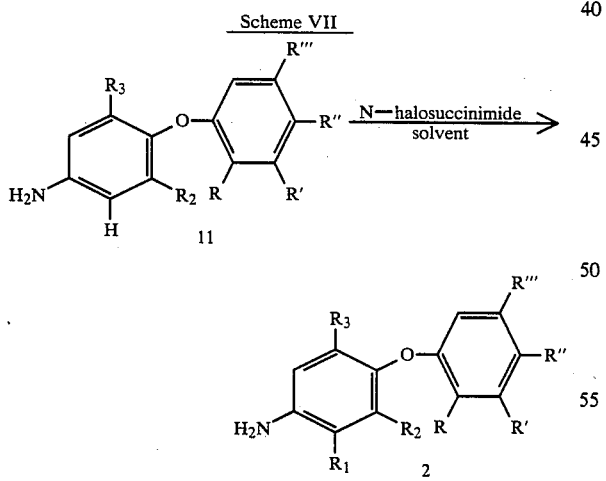

wherein $R_1$, $R_2$, $R_3$, R, R', R" and R'" have the meaning given in Formula (1).

The substituted phenoxyanilines 2 for which $R_1$ is chlorine or bromine are obtained upon halogenation of 3,5-disubstituted-4-phenoxyaniline 11 as depicted in Scheme VII below as follows:

wherein $R_1$ is chlorine or bromine and $R_2$, $R_3$, R, R', R" and R'" have the meaning given in Formula (1). Suitable solvents for this transformation include haloalkanes; aromatic hydrocarbons, such as benzene; or polar protic solvents, such as acetic acid. Halogenation of aniline 11 may be effected by its exposure to chlorine or bromine in a suitable solvent at low temperature or preferably treatment with a N-halosuccinimide in benzene. Temperatures required for the reaction vary according to the identity of substituents $R_2$ and $R_3$ but generally fall in the range of 25° C.–80° C.

Phenoxyanilines of type 11 are prepared by the method depicted in Scheme V above making use of the 3,4,5-trisubstituted nitrobenzene 12 as the electrophilic component in this coupling reaction. Chloronitrobenzenes of type 12 are illustrated as follows:

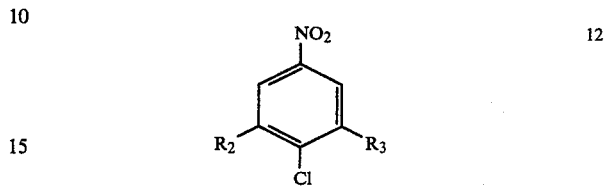

wherein $R_2$ and $R_3$ have the meaning given in Formula (1). Chloronitrobenzenes of type 12 are obtained from the corresponding nitroanilines via the Sandmeyer procedure as practiced by Miller et. al. *J. Med. Chem.* 23, 1083 (1980).

Alternatively, chloronitrobenzenes of type 8 can be prepared through the nitration of a chlorobenzene as typified by the synthesis of 3,4-dichloro-2,5-dimethylnitrobenzene 16 illustrated in Scheme VIII as follows:

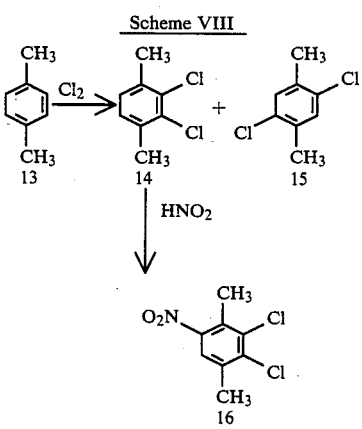

The preparation of phenols of type 9 is illustrated by the elaboration of 4-bromo-2-fluorophenol from 2-fluorophenol using the procedure set forth by Mitchell et al., *J. Org. Chem.*, 25, 4733 (1979). Another phenolic intermediate, 2-bromo-4-chlorophenol, is obtained analogously from 4-chlorophenol.

An alternate route to phenoxyanilines of type 2, in particular the phenoxyaniline 21, is depicted in Scheme IX below as follows:

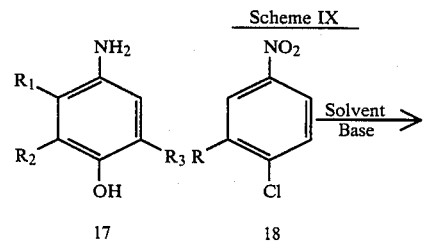

-continued
Scheme IX

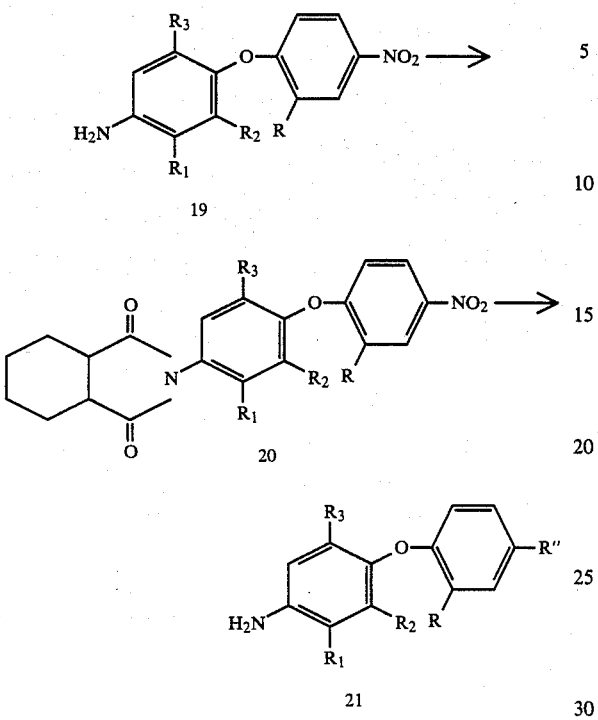

wherein R₁, R₂, R₃, R and R" have the meaning given in Formula (1) and R" is chlorine or bromine. This reaction involves the coupling of an aminophenol 17 with a 4-chloronitrobenzene 18 in the presence of a base to afford 4-nitrophenoxyaniline 19 as described in Schramm et al., *Ann.*, 740, 169 (1970). Reaction of the amino group in 19 with cyclohexane 1,2-dicarboxylic anhydride affords imide 20. Nitro group reduction, Sandmeyer halogenation and deprotection of the amino function afford aniline 21. The details of these transformations are given in the experimental section hereinbelow.

Aminophenols of type 17 are readily available and may be prepared as illustrated in the elaboration of aminophenol 25 via nitration of a 2,5-disubstituted phenol 22 followed by halogenation and nitro group reduction as depicted in Scheme X below as follows:

Scheme X

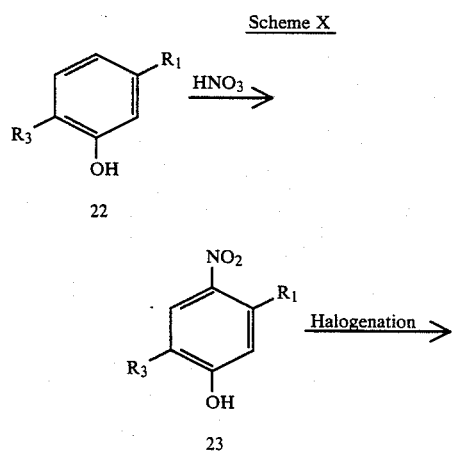

-continued
Scheme X

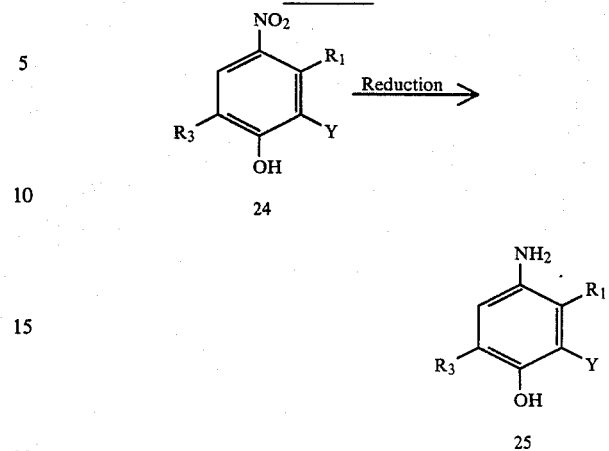

wherein R₁ and R₃ have the meaning given in Formula (1) and Y is bromine or chlorine. This approach to intermediates 23 and 24 reflect that described by Albert and Sears, *J. Am. Chem. Soc.*, 76, 4979 (1954).

An alternate and complimentary approach to aminophenols 17 is detailed in Scheme XI as follows:

Scheme XI

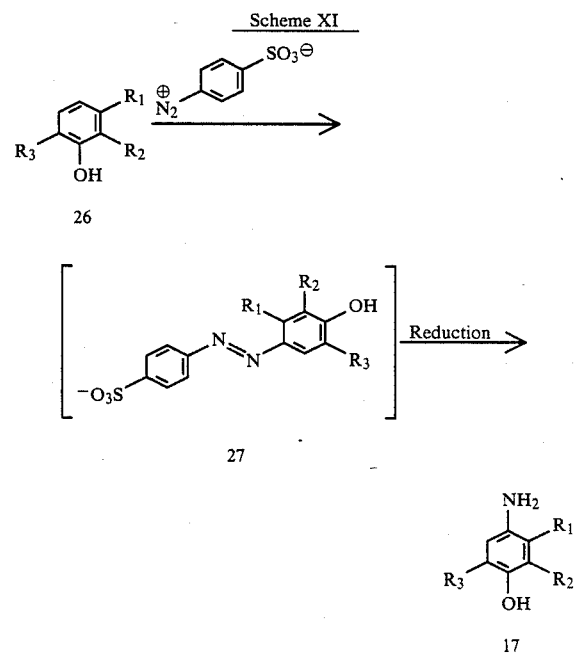

wherein R₁, R₂ and R₃ have the meaning given in Formula (1). This involves the reaction of a trisubstituted phenol 26 with a diazonium salt prepared from sulfanilic acid to afford the intermediate diazo compound 27 which is reduced to give aminophenol 17. The synthetic methodology used in this approach to aminophenol 17 is that described by Payne and Weiden in U.S. Pat. No. 3,752,838.

The compounds contemplated in this invention may be employed as insecticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, nitrobenzene, cyclohexanone or dimethylformamide and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fuller's earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seed, or the roots of plants without injuring either the seeds or roots of plants. Mixtures of the active compounds may be employed if desired as well as combinations of the active compounds of this invention with other biologically active compounds or ingredients.

The following examples are illustrative of the methods utilized in the preparation of intermediates and compounds of this invention. For NMR spectroscopic analysis, chemical shifts are reported in parts per million downfield from TMS.

EXAMPLE A

Preparation of 4-(2,4-difluorophenoxy)-2,3,5-trichloroaniline

Into a 300 milliliter round bottom reaction flask was charged 14.9 grams (51.4 mmol) of 3,5-dichloro-4-(2,4-difluorophenoxy) aniline, 7.2 grams (53.9 mmol) of N-chlorosuccinimide (NCS), and 100 milliliters of benzene. The reaction mixture was refluxed for 2 hours after which time additional NCS (350 milligrams, 2.6 mmol) was added. Reflux was then continued for an additional 1 hour. The mixture was allowed to cool, diluted with ethyl acetate (200 milliliters), washed with $H_2O$, saturated $NaHCO_3$ and brine; dried over $Na_2SO_4$ and concentrated under reduced pressure. The oily product obtained was purified by flash column chromatography (1:1 hexane toluene) to afford 4-(2,4-difluorophenoxy)-2,3,5-trichloroaniline (9.8 grams, 30.2 mmol, 59%) as a dark brown oil. The structure of this material was verified by its H'-NMR spectrum ($CDCl_3$) 7.30–6.10 (m, 3H), 6.75 (s, 1H), 4.18 (br s, 2H).

EXAMPLE B

Preparation of 2-chloro-4-(2,4-dichlorophenoxy)-3,5-dimethylaniline

Into a 200 milliliter three-necked, round bottom reaction flask was charged 6.76 grams (24.0 mmol) of 4-(2,4-dichlorophenoxy)-3,5-dimethyl aniline and 48 milliliters of benzene. N-chlorosuccinimide (3.85 grams, 28.8 mmol) was then added and the resultant heterogeneous mixture was stirred at room temperature for 1 hour. The reaction mixture was diluted with ethyl acetate, washed (2x) with saturated $Na_2SO_3$ solution and dried over $Na_2SO_4$. Concentration under reduced pressure afforded the crude product as a dark oil. This material was filtered through a short column of silica gel using 9:1 hexane: ethyl acetate as an eluant. Solvent removal under reduced pressure afforded 2-chloro-4-(2,4-dichlorophenoxy)-3,5-dimethylaniline (6.5 grams) contaminated with at least three other products. This material was placed in a Parr bottle and dissolved in toluene (50 milliliters). The Parr bottle was purged with nitrogen, 5% platinum on carbon (650 milligrams) was added and the mixture was hydrogenated for 1 hour at 40–50 psi and room temperature on a rocking Parr hydrogenator. Filtration through a pad of celite, solvent removal and flash chromatography (9:1 hexane: ethyl acetate afforded pure 2-chloro-4-(2,4-dichlorophenoxy)-3,5-dimethyl aniline (3.1 grams, 9.8 mmol, 41%) as a crystallized solid having a melting point of 89° C.–93° C. Elemental analysis of the crystalline solid indicated the following:

Analysis: $C_{14}H_{12}Cl_3NO$
Calculated: C, 53.11; H, 3.82; N, 4.42.
Found: C, 53.38; H, 3.98; N, 4:30.

EXAMPLE C

Preparation of 2,5-dichloro-4-(2,4-dichlorophenoxy)-3-methylaniline
and
2,3-dichloro-4-(2,4-dichlorophenoxy)-5-methylaniline Into a magnetically stirred solution of 3-chloro-4-(2,4-dichlorophenoxy)-5-methylaniline (9.0 grams, 29.7 mmol) in benzene (60 milliliters) was added solid N-chlorosuccinimide (4.4 grams, 32.7 mmol). The mixture was stirred at room temperature for 1.5 hours, transferred to a separatory funnel and washed with saturated Na$_2$SO$_3$ solution (3x), water (2x) and brine (1x). The organic layer was dried over Na$_2$SO$_4$ and concentrated under reduced pressure to afford the crude product (10.08 grams) as a dark brown oil. Flash column chromatography on 500 grams of silica gel (3:1 hexane:ethyl acetate) afforded pure 2,5-dichloro-4-(2,4-dichlorophenoxy)-3-methylaniline (2.85 grams, 7.4 mmol, 25%) having a melting point of 96° C.–97° C. and 2,3-dichloro-4-(2,4-dichlorophenoxy)-5-methylaniline (2.16 grams, 6.4 mmol, 22%) having a melting point of 95° C. Recrystallization from methanol afforded analytical samples. Elemental analysis of the samples indicated the following:

Analysis: C$_{13}$H$_9$Cl$_4$NO
Calculated: C, 46,32; H, 2.69; N, 4.15.
Found (2,5-dichloro-): C, 46.30; H, 2.54; N, 4.16.
Found (2,3-dichloro-): C, 46.18; H, 2.72; N, 4.02.

EXAMPLE D

Preparation of 2-bromo-4-(2-bromo-4-chlorophenoxy)-3,5-dichloroaniline

Into a magnetically stirred solution of 4-(2-bromo-4-chlorophenoxy)-3,5-dichloroaniline (6.38 grams, 17.36 mmol) in benzene (35 milliliters) was added N-bromosuccinimide (3.71 grams, 20.83 mmol). The reaction mixture was stirred for two hours at room temperature, transferred to a separatory funnel and washed with saturated Na$_2$SO$_3$ solution (2x), water (2x) and brine (1x). The organic layer was dried over Na$_2$SO$_4$ and concentrated under reduced pressure to afford the crude product which when subjected to flash column chromatography on 760 grams of silica gel (4:1 hexane:ethyl acetate) afforded pure 2-bromo-4-(2-bromo-4-chlorophenoxy)-3,5-dichloroaniline (5.15 grams, 11.53 mmol, 66%). Elemental analysis of the product indicated the following:

Analysis: C$_{12}$H$_6$Br$_2$Cl$_3$NO
Calculated: C, 32.28; H, 1.35; N, 3:13.
Found: C, 32.48; H, 1.24; N, 2.92.

EXAMPLE E

Preparation of 4-amino-2,3,6-trimethylphenol

Into a solution of sulfanilic acid (13.0 grams, 68 mmol) in water (68 milliliters) contained in a 250 milliliter round bottom flask equipped with a magnetic stirrer, internal thermometer and ice bath at 15° C. was added solid Na$_2$CO$_3$ (3.69 grams, 34 mmol) followed by a solution of NaNO$_2$ (5.1 grams, 74 mmol) in water (14 milliliters). The latter addition caused a color change from milky-white to orange. A separate 500 milliliter three-necked flask equipped with a magnetic stirrer, internal thermometer and ice bath was charged with concentrated hydrochloric acid (12 milliliters), ice (68 grams) and the solution of the diazonium salt prepared above. This mixture was stirred at 15° C. for 45 minutes. Meanwhile a third flask (1 L) equipped with an internal thermometer, nitrogen inlet, condenser, addition funnel and mechanical stirrer was charged with water (68 milliliters), NaOH (14.96 grams, 318 mmol) and 2,3,6-trimethylphenol (9.30 grams, 68 mmol). This mixture was cooled to 0° C. by means of an ice-salt mixture and the diazonium salt - hydrochloric acid mixture prepared above was added dropwise while maintaining the temperature below 5° C. Upon completion of the diazonium salt addition the reaction mixture was warmed to 52° C. and solid Na$_2$S$_2$O$_4$ (3.13 grams, 18 mmol) was added. Stirring was continued and the mixture heated to 80° C. whereupon additional Na$_2$S$_2$O$_4$ (28.2 grams, 162 mmol) was added in three equal portions (9.4 grams each) at 5 minute intervals. The mixture was heated at 80° C. under nitrogen for 20 minutes, cooled to room temperature and filtered to afford the crude product as a yellow solid. The solid was dissolved in ethyl acetate (300 milliliters) and washed with water. The organic layer was dried over Na$_2$SO$_4$ and concentrated under reduced pressure to afford 4-amino-2,3,6-trimethylphenol in quantitative yield which was used successfully in subsequent reactions without further purification. H'-NMR (CDCl$_3$) 6.30 (S, 1H), 2.11 (S, 9H).

EXAMPLE 1

Preparation of 1-[3-Chloro-4-(2,4-dichlorophenoxy)-2,5-dimethylphenyl]-3-(2,6-difluorobenzoyl)urea Part A: Preparation of 3-chloro-4-(2,4-dichlorophenoxy)-2,5-dimethylnitrobenzene Into a 250 milliter three-necked round bottom reaction flask equipped with a magnetic stirrer and nitrogen inlet was charged 10.0 grams (45.44 mmol) of 3,4-dichloro-2,5-dimethylnitrobenzene, 7.95 grams (48.81 mmol) of 2,4-dichlorophenol, 9.41 grams (68.11 mmol) of potassium carbonate and 60 milliliters dimethylformamide. The reaction mixture was stirred and heated at a temperature of 100° C. for a period of 20 hours and then cooled to room temperature, filtered and concentrated under reduced pressure. The residue was diluted with methylene chloride and the organic layer was washed with 4% NaOH solution (2x) and brine, dried through Na$_2$SO$_4$ and concentrated under reduced pressure to afford the crude product as a dark brown, viscous liquid. The addition of hexane and ethyl acetate afforded a light brown solid which was subjected to Kugelrohr distillation (about 180° C. and about 0.1 mm mercury) to give pure 3-chloro-4-(2,4-dichlorophenoxy)-2,5-dimethylnitrobenzene (7.17 grams, 20.7 mmol, 45%) as a yellow solid having a melting point of 118° C.–121° C. NMR spectroscopic analysis indicated the following: H'-NMR (CDCl$_3$) 7.76 (br S, 1H), 7.53 (d, J=2 Hz, 1H), 7.12 (d,d; 2.9 Hz; 1H), 6.34 (d, J=9 Hz, 1H), 2.45 (S, 3H), 2.24 (S, 3H).

Part B: Preparation of 3-chloro-4-(2,4-dichlorophenoxy)-2,5-dimethylaniline

Into a 250 milliliter Parr bottle was charged 6.59 grams (19.01 mmol) of 3-chloro-4-(2,4-dichlorophenoxy)-2,5-dimethylnitrobenzene prepared in Part A and 15 milliliters of toluene. The bottle was purged with nitrogen and solid 10% platinum on carbon (650 milligrams) was added. The reaction mixture was then hydrogenated for 45 minutes at 43–47 psi hydrogen and room temperature on a rocking Parr hydrogenator. The catalyst was removed by filtration through celite and the filtrate was concentrated under reduced pressure to afford the product as a thick yellow oil. The addition of hexane afforded pure 3-chloro-4-(2,4-dichlorophenoxy)-2,5-dimethylaniline (4.82 grams, 15.22 mmol, 80%) as a white powder. NMR spectroscopic analysis indicated the following: H'-NMR (CDCl$_3$) 7.36 (d, J=2H, 1H), 6.95 (d,d; J=2.9 Hz; 1H), 6.40 (br s, 1H), 6.32 (d, J=9 Hz, 1H), 3.54 (br s, 2H), 2.15 (s, 3H), 2.02 (s, 3H).

Part C: Preparation of 1-[3-chloro-4-(2,4-dichlorophenoxy)-2,5-dimethylphenyl]-3-(2,6-difluorobenzoyl)urea Into a magnetically stirred solution of 3-chloro-4-(2,4-dichlorophenoxy)-2,5-dimethylaniline (1.5 grams, 4.73 mmol) prepared in Part B in toluene (15 milliliters) under nitrogen atmosphere was added neat 2,6-difluorobenzoyl isocyanate (1.3 grams, 7.10 mmol) and the mixture was refluxed for a period of 1 hour. The reaction mixture was allowed to cool and hexane (3 milliliters) was added to induce crystallization. The resultant precipitate was filtered and washed successively with hexane and toluene to give pure 1-[3-chloro-4-(2,4-dichlorophenoxy)-2,5-dimethylphenyl]-3-(2,6-difluorobenzoyl) urea (2.29 grams, 4.58 mmol, 97%) as a white solid having a melting point of 188° C.–190° C. Elemental analysis of the white solid indicated the following:

Analysis: $C_{22}H_{15}Cl_3F_2N_2O_3$
Calculated: C, 52.87; H, 3.03; N, 5.61.
Found: C, 52.91; H, 3.07; N, 5.65

EXAMPLE 2

Preparation of 1-[3-Bromo-4-(2,4-dichlorophenoxy)-2,5-dimethylphenyl]-3-(2,6-difluorobenzoyl)urea

Part A: Preparation of 2-bromo-3,6-dimethyl-4-nitrophenol

Into a magnetically stirred suspension of 2,5-dimethyl-4-nitrophenol (12.70 grams, 75.98 mmol) in $CH_2Cl_2$ (150 milliliters) at room temperature was added portionwise N-bromosuccinimide (14.88 grams, 83.58 mmol). The mixture rapidly became homogeneous and after one hour thin layer chromatography (3:1 hexane:ethyl acetate) indicated complete consumption of the starting material and formation of a single major product. Saturated $Na_2SO_3$ solution (15 milliliters) was added and the solvent was removed under reduced pressure. Ethyl acetate was then added and the organic layer was washed with water and brine, dried over $Na_2SO_4$ and concentrated under reduced pressure to afford 2-bromo-3,6-dimethyl-4-nitrophenol (13.6 grams, 55.3 mmol, 73%) as a rust colored solid. H'-NMR ($CDCl_3$) 9.26 (brS, 1H), 7.71 (S, 1H), 2.60 (S, 3H), 2.31 (S, 3H).

Part B: Preparation of 4-amino-2-bromo-3,6-dimethylphenol

Into a Parr bottle was charged 2-bromo-3,6-dimethyl-4-nitrophenol (13.6 grams, 55.3 mmol) prepared in Part A and ethyl acetate (50 milliliters). The reaction vessel was purged with nitrogen and 5% platinum on carbon (1.36 grams) was added immediately following the purge. Hydrogenation was carried out on a rocking Parr hydrogenator for 1.5 hours at 40–50 psi hydrogen and room temperature. The reaction mixture was filtered through celite and concentrated under reduced pressure to give 4-amino-2-bromo-3,6-dimethylphenol as a brown solid in quantitative yield. H'-NMR ($CDCl_3$-$DMSO$-$d_6$), 6.40 (S, 1H), 2.17 (brS, 6H).

Part C: Preparation of 3-bromo-4-(2-chloro-4-nitrophenoxy)-2,5-dimethylaniline Into a dry 250 milliliter round bottom flask equipped with a magnetic stirrer and nitrogen inlet was added 4-amino-2-bromo-3,6-dimethylphenol (11.94 grams, 55.3 mmol) prepared in Part B and dry dimethylsulfoxide (118 milliliters). Potassium t-butoxide (7.26 grams, 64.65 mmol) was added portionwise under nitrogen and the mixture was stirred at room temperature for 0.5 hours. Solid 3,4-dichloronitrobenzene (13.33 grams, 70.52 mmol) was then added and the reaction mixture was heated at 50° C. for 48 hours. After cooling the mixture was diluted with toluene and washed successively with saturated $NH_4Cl$ solution (3x) and with 5% NaOH solution until the aqueous washes remained colorless. This was followed by washes with water and brine, drying over $Na_2SO_4$ and solvent removal under reduced pressure to afford the crude product (9.4 grams) as a dark red-brown oil. Flash column chromatography on 650 grams of silica gel (3:1 hexane:ethyl acetate) afforded pure 3-bromo-4-(2-chloro-4-nitrophenoxy)-2,5-dimethylaniline (4.7 grams, 12.6 mmol, 23%) as a yellow-brown solid. H'-NMR ($CDCl_3$) 8.42 (d, J=2 Hz, 1H), 8.01 (d,d; J=2, 9 Hz; 1H), 6.55 (d, J=9 Hz, 1H), 6.58 (S, 1H), 3.73 (brS, 2H), 2.28 (S, 3H), 2.06 (S, 3H).

Part D: Preparation of 8-[3-bromo-4-(2-chloro-4-nitrophenoxy)-2,5-dimethylphenyl]-8-azabicyclo[4.3.0]-nonan-7,9-dione To a solution of 3-bromo-4-(2-chloro-4-nitrophenoxy)-2,5-dimethylaniline (4.7 grams, 12.65 mmol) prepared in Part C in toluene (40 milliliters) was added cis-1,2-cyclohexane dicarboxylic anhydride (20.48 grams, 132.83 mmol) and a spatula tipful of toluene sulfonic acid. The reaction mixture was heated at reflux overnight and allowed to cool; washed with 5% NaOH solution (5x), water (3x) and brine (1x); dried over $Na_2SO_4$ and concentrated under reduced pressure to afford the crude desired product as a thick brown oil (5.43 grams, 10.69 mmol, 84%) which crystallized on standing and had a melting point of 187° C.–190° C. H'-NMR ($CDCl_3$) 8.40 (d, J=2 Hz, 1H), 8.02 (d,d; J=2, 9 Hz, 1H), 7.00 (br, 5, 1H), 6.55 (d, J=9 Hz, 1H), 3.10 (M, 2H), 2.21 (brS, 6H), 1.93 (M, 4H), 1.58 (m, 4H).

Part E: Preparation of 8-[4-(4-amino-2-chlorophenoxy)-3-bromo-2,5-dimethylphenyl]-8-azabicyclo[4.3.0]-nonan-7,9-dione Into a Parr bottle was charged 8-[3-bromo-4-(2-chloro-4-nitrophenoxy)-2,5-dimethylphenyl]-8-azabicyclo[4.3.0]-nonan-7,9-dione (3.45 grams, 6.79 mmol) prepared in Part D and ethyl acetate (100 milliliters). The reaction mixture was purged with nitrogen, 5% platinum on carbon (480 milligrams) was added and the mixture was hydrogenated for 1.5 hours at 40–50 psi hydrogen and room temperature on a rocking Parr hydrogenator. Filtration through celite and concentration under reduced pressure afforded the desired product (2.73 grams, 5.71 mmol, 84%). H'-NMR ($CDCl_3$) 6.93 (br s, 1H), 6.80 (d, J=2 Hz, 1H), 6.33 (m, 2H), 3.45 (br s, 2H), 3.06 (br m, 2H) 2.4–1.2 (m, 14H).

Part F: Preparation of 3-bromo-4-(2,4-dichlorophenoxy)-2,5-dimethyl aniline Into an ice-chilled, magnetically stirred solution of $NaNO_2$ (420 milligrams, 6.07 mmol) in concentrated sulfuric acid (3.0 milliliters) was added dropwise a solution of 8-[4-(4-amino-2-chlorophenoxy)-3-bromo-2,5-dimethylphenyl]-8-azabicyclo [4.3.0] nonan-7,9-dione (2.66 grams, 5.57 mmol) prepared in Part E in acetic acid (14 milliliters) keeping the internal temperature below 15° C. The reaction mixture was stirred for 15 minutes at 15° C. and then for 2 hours at ambient temperature. During this latter time period a solution of cuprous chloride was prepared as follows: to a solution prepared from $CuSO_4 \cdot (H_2O)_5$ (4.85 grams, 19.44 mmol), NaCl (830 milligrams, 14.20 mmol) and water (22 milliliters) was added under nitrogen a solution prepared from $NaHSO_3$ (780 milligrams, 7.46 mmol), NaOH (450 milligrams, 9.56 mmol) and water (4 milliliters). The mixture was swirled and the supernatant liquid was decanted off. The cream colored precipitate was washed with water (3x) until the decanted supernatant liquid was colorless. Concentrated hydrochloric acid (12 milliliters) was then added affording a pale green solution containing cuprous chloride. To this solution was added dropwise the diazonium salt in acetic acid/$H_2SO_4$ and the mixture was stirred for 0.5 hours. The reaction mixture was diluted with ethyl acetate and washed with saturated $Na_2SO_3$ solution, water and brine; dried over $Na_2SO_4$ and concentrated under reduced pressure to afford crude product (2.4 grams, 4.8 mmol, 86%) as a gold solid.

The crude product (2.0 grams, 4.02 mmol) was dissolved in methanol (8 milliliters) and hydrazine monohydrate (20.1 grams, 402 mmol) was added dropwise. The mixture was heated at reflux for 48 hours, cooled and diluted with ethyl acetate and water. Aqueous hydrochloric acid (2%) was added until the aqueous phase became homogeneous. The organic layer was then washed with water (3x) and brine, dried over $Na_2SO_4$ and concentrated under reduced pressure to afford the desired product (1.10 grams, 3.05 mmol, 76%) as an orange oil which slowly crystallized on standing. H'-NMR ($CDCl_3$) 7.45 (d, J=2 Hz, 1H), 7.05 (d, d; J=2, 9 Hz; 1H), 6.54 (brS, 1H), 6.37 (d, J=9 Hz, 1H), 3.63 (brS, 2H), 2.26 (S, 3H), 2.06 (S, 3H).

Part G: Preparation of 1-(3-bromo-4-(2,4-dichlorophenoxy)-2,5-dimethylphenyl)-3-(2,6-difluorobenzoyl)urea Into a magnetically stirred solution of 3-bromo-4-(2-4-dichlorophenoxy)-2,5-dimethylaniline (960 milligrams, 2.67 mmol) prepared in Part F in 1:1 hexane:toluene (5 milliliters) was added neat 2,6-difluorobenzoyl isocyanate (490 milligrams, 2.67 mmol) and the mixture was stirred under a nitrogen atmosphere for 10 minutes. The resultant precipitate was collected on a filtered funnel, washed with toluene and dried to afford the desired product (1.26 grams, 2.3 mmol, 87%) as an off-white powder having a meting point of 205° C.–209° C. NMR spectroscopic analysis indicated the following: H'-NMR ($CDCl_3$) 11.60 (br s, 1H), 10.17 (br s, 1H), 8.00–7.10 (m, 6H), 6.43 (d, J=9 Hz, 1H), 2.39 (s, 3H), 2.11 (s, 3H).

EXAMPLES 3–102

In a manner similar to that employed in the preceding examples, and using one of the synthesis schemes previously disclosed, other urea compounds were prepared. The identity of the substituents on the generic formula and the analytical data are set forth in Table I below:

TABLE I

Representative 1-(4-Phenoxyphenyl)-3-Benzoyl Urea Compounds

| Example | Molecular Formula | X | X' | X'' | $R_1$ | $R_2$ | $R_3$ | R | R' | R'' | R''' | C (Calc) | H (Calc) | N (Calc) | C (Found) | H (Found) | N (Found) | Melting Point °C |
|---|---|---|---|---|---|---|---|---|---|---|---|---|---|---|---|---|---|---|
| 3 | $C_{20}H_9Cl_5F_2N_2O_3$ | F | F | H | Cl | Cl | Cl | Cl | H | Cl | H | 44.43 | 1.67 | 5.18 | 44.43 | 1.77 | 5.14 | 203–204 |
| 4 | $C_{23}H_{18}Cl_2F_2N_2O_3$ | F | F | H | $CH_3$ | $CH_3$ | $CH_3$ | Cl | H | Cl | H | 57.64 | 3.79 | 5.85 | 57.91 | 3.94 | 5.72 | 199.5–204 |
| 5 | $C_{21}H_{12}Cl_4F_2N_2O_3$ | F | F | H | Cl | Cl | $CH_3$ | Cl | H | Cl | H | 48.49 | 2.33 | 5.39 | 48.18 | 2.35 | 5.29 | 205–206 |
| 6 | $C_{21}H_{12}Cl_4F_2N_2O_3$ | F | F | H | Cl | $CH_3$ | Cl | Cl | H | Cl | H | 48.49 | 2.33 | 5.39 | 48.67 | 2.47 | 5.25 | 209–211 |
| 7 | $C_{22}H_{15}Cl_3F_2N_2O_3$ | F | F | H | Cl | $CH_3$ | $CH_3$ | Cl | H | Cl | H | 52.87 | 3.03 | 5.61 | 52.88 | 3.09 | 5.58 | 212–214 |
| 8 | $C_{20}H_{10}Cl_6N_2O_3$ | Cl | H | H | Cl | Cl | Cl | Cl | H | Cl | H | 44.57 | 1.87 | 5.70 | 44.52 | 1.84 | 5.03 | 203–205 |
| 9 | $C_{22}H_{16}Cl_4N_2O_3$ | Cl | H | H | $CH_3$ | Cl | $CH_3$ | Cl | H | Cl | H | 53.04 | 3.24 | 5.62 | 52.91 | 3.26 | 5.60 | 179–181 |
| 10 | $C_{22}H_{16}Cl_4N_2O_3$ | Cl | H | H | Cl | $CH_3$ | $CH_3$ | Cl | H | Cl | H | 53.04 | 3.24 | 5.62 | 52.64 | 3.21 | 5.84 | 184–187 |
| 11 | $C_{20}H_9Cl_6F_1N_2O_3$ | Cl | F | H | Cl | Cl | Cl | Cl | H | Cl | H | 43.13 | 1.63 | 5.03 | 42.57 | 1.87 | 4.91 | 224–226 |
| 12 | $C_{22}H_{15}Cl_4F_1N_2O_3$ | Cl | F | H | $CH_3$ | Cl | $CH_3$ | Cl | H | Cl | H | 51.19 | 2.93 | 5.43 | 51.70 | 2.96 | 5.32 | 208.5–210 |
| 13 | $C_{21}H_{15}Cl_5N_2O_3$ | Cl | H | H | Cl | $CH_3$ | $CH_3$ | Cl | H | Cl | H | 49.61 | 2.84 | 5.26 | 49.81 | 2.92 | 5.32 | 218–220 |
| 14 | $C_{22}H_{16}Cl_3F_1N_2O_3$ | F | Cl | H | $CH_3$ | Cl | $CH_3$ | Cl | H | Cl | H | 54.85 | 3.35 | 5.81 | 54.87 | 3.40 | 5.74 | 165–168 |
| 15 | $C_{22}H_{16}Cl_3F_1N_2O_3$ | Cl | H | 5-F | $CH_3$ | Cl | $CH_3$ | Cl | H | Cl | H | 54.85 | 3.35 | 5.81 | 55.06 | 3.38 | 5.78 | 166–166.5 |
| 16 | $C_{22}H_{15}Cl_4F_1N_2O_3$ | Cl | H | H | Cl | Cl | $CH_3$ | Cl | H | Cl | H | 51.19 | 2.92 | 5.43 | 51.01 | 3.88 | 5.50 | 175–176 |
| 17 | $C_{22}H_{15}Cl_4F_1N_2O_3$ | Cl | H | 4-F | $CH_3$ | Cl | $CH_3$ | Cl | H | Cl | H | 51.19 | 2.92 | 5.43 | 50.60 | 3.03 | 5.44 | 198–199 |
| 18 | $C_{20}H_9Br_1Cl_4F_2N_2O_3$ | F | F | H | Cl | Cl | Cl | Br | H | Cl | H | 41.06 | 1.55 | 4.79 | 40.96 | 1.50 | 4.75 | 204.5–206 |
| 19 | $C_{20}H_9Br_2Cl_3F_2N_2O_3$ | F | F | H | Cl | Cl | Cl | Br | H | Br | H | 38.16 | 1.44 | 4.45 | 38.38 | 1.38 | 4.37 | 204–207 |
| 20 | $C_{22}H_{15}Br_1Cl_2F_2N_2O_3$ | F | F | H | $CH_3$ | Cl | $CH_3$ | Br | H | Cl | H | 48.56 | 2.78 | 5.15 | 48.55 | 2.82 | 5.08 | 215–217 |
| 21 | $C_{22}H_{15}Br_1Cl_2F_2N_2O_3$ | F | F | H | Cl | $CH_3$ | $CH_3$ | Br | H | Cl | H | 48.56 | 2.78 | 5.15 | 49.49 | 2.99 | 5.30 | 190.5–191.5 |
| 22 | $C_{20}H_{10}Br_1Cl_5N_2O_3$ | Cl | H | H | Cl | Cl | Cl | Br | H | Cl | H | 41.17 | 1.73 | 4.80 | 40.63 | 1.57 | 4.85 | 199–200.5 |
| 23 | $C_{20}H_9Br_2Cl_4N_2O_3$ | Cl | H | H | Cl | Cl | Cl | Br | H | Br | H | 38.26 | 1.61 | 4.46 | 38.26 | 1.59 | 4.37 | 205.5–207.5 |
| 24 | $C_{22}H_{16}Br_1Cl_3N_2O_3$ | Cl | H | H | $CH_3$ | Cl | $CH_3$ | Br | H | Cl | H | 48.70 | 2.97 | 5.16 | 49.20 | 3.08 | 5.16 | 190–190.5 |
| 25 | $C_{22}H_{16}Br_1Cl_3N_2O_3$ | Cl | H | H | Cl | $CH_3$ | $CH_3$ | Br | H | Cl | H | 42.37 | 1.78 | 4.94 | 42.52 | 1.91 | 4.82 | 183.5–186 |
| 26 | $C_{20}H_{10}Br_2Cl_3F_1N_2O_3$ | Cl | F | H | Cl | Cl | Cl | Br | H | Br | H | 39.29 | 1.65 | 4.58 | 39.32 | 1.83 | 4.46 | 192–195 |
| 27 | $C_{22}H_{16}Br_1Cl_2F_1N_2O_3$ | Cl | F | H | Cl | Cl | $CH_3$ | Br | H | Cl | H | 50.22 | 3.06 | 5.32 | 50.02 | 3.08 | 5.25 | 161.5–164 |
| 28 | $C_{22}H_{16}Br_1Cl_2F_1N_2O_3$ | Cl | F | H | $CH_3$ | $CH_3$ | Cl | Br | H | Cl | H | 50.22 | 3.06 | 5.32 | 50.16 | 3.14 | 5.30 | 168.5–170 |
| 29 | $C_{22}H_{15}Br_1Cl_3F_1N_2O_3$ | F | F | H | $CH_3$ | Cl | $CH_3$ | Br | H | Br | H | 47.13 | 2.71 | 4.99 | 47.92 | 2.84 | 4.85 | 230–231 |
| 30 | $C_{22}H_{15}Br_2Cl_1F_2N_2O_3$ | F | F | H | $CH_3$ | Cl | $CH_3$ | Br | H | Br | H | 44.88 | 2.57 | 4.76 | 44.89 | 2.62 | 4.64 | 196–197 |
| 31 | $C_{22}H_{16}Br_2Cl_2N_2O_3$ | Cl | H | H | $CH_3$ | Cl | $CH_3$ | Br | H | Br | H | 45.00 | 2.75 | 4.77 | 45.26 | 2.74 | 4.70 | 194–197 |
| 32 | $C_{22}H_{16}Br_2Cl_1F_1N_2O_3$ | Cl | F | H | $CH_3$ | Cl | $CH_3$ | Br | H | Br | H | 46.32 | 2.83 | 4.91 | 46.26 | 2.69 | 4.89 | 191–194 |
| 33 | $C_{22}H_{15}Br_2Cl_2F_1N_2O_3$ | F | F | H | $CH_3$ | Cl | $CH_3$ | F | H | Br | H | 43.67 | 2.50 | 4.63 | 44.08 | 2.56 | 4.55 | 215–218 |
| 34 | $C_{20}H_9Cl_3F_4N_2O_3$ | F | F | H | Cl | Cl | Cl | F | H | F | H | 47.32 | 1.79 | 5.52 | 47.11 | 1.84 | 5.36 | 211–213 |
| 35 | $C_{22}H_{15}Cl_1F_4N_2O_3$ | F | F | H | $CH_3$ | Cl | $CH_3$ | F | H | F | H | 56.60 | 3.24 | 6.00 | 56.77 | 3.25 | 6.04 | 153–154 |
| 36 | $C_{20}H_{10}Cl_4F_2N_2O_3$ | F | F | H | Cl | Cl | Cl | F | H | Cl | H | 47.47 | 1.99 | 5.54 | 47.46 | 2.01 | 5.45 | 180–183 |
| 37 | $C_{22}H_{16}Cl_2F_2N_2O_3$ | F | F | H | $CH_3$ | Cl | $CH_3$ | F | H | F | H | 56.79 | 3.47 | 6.02 | 57.61 | 3.66 | 6.28 | 166–168 |
| 38 | $C_{22}H_{15}Cl_3F_2N_2O_3$ | Cl | H | H | $CH_3$ | Cl | $CH_3$ | Cl | H | F | H | 52.87 | 3.03 | 5.61 | 53.15 | 3.21 | 5.50 | 186–188 |
| 39 | $C_{22}H_{16}Cl_1F_3N_2O_3$ | F | F | H | $CH_3$ | Cl | $CH_3$ | F | H | Cl | H | 58.87 | 3.59 | 6.24 | 59.13 | 3.61 | 6.28 | 173–174 |
| 40 | $C_{22}H_{15}Cl_2F_3N_2O_3$ | F | F | H | $CH_3$ | Cl | $CH_3$ | Cl | H | F | H | 54.68 | 3.13 | 5.80 | 54.52 | 3.03 | 5.81 | 206–207.5 |
| 41 | $C_{22}H_{16}Cl_3F_1N_2O_3$ | Cl | H | H | $CH_3$ | Cl | $CH_3$ | Cl | H | F | H | 54.85 | 3.35 | 5.81 | 54.37 | 3.31 | 5.61 | 204.5–205 |

TABLE I-continued

Representative 1-(4-Phenoxyphenyl)-3-Benzoyl Urea Compounds

| Example | Molecular Formula | X | X' | X'' | R₁ | R₂ | R₃ | R | R' | R'' | R''' | Elemental Analysis Calculated C | H | N | Found C | H | N | Melting Point °C. |
|---|---|---|---|---|---|---|---|---|---|---|---|---|---|---|---|---|---|---|
| 42 | C₂₂H₁₅BrClF₃N₂O₃ | F | F | H | CH₃ | Cl | CH₃ | F | H | Br | H | 50.07 | 2.87 | 5.31 | 50.02 | 3.02 | 5.12 | 189–190 |
| 43 | C₂₂H₁₆BrCl₂F₁N₂O₃ | Cl | F | H | CH₃ | Cl | CH₃ | F | H | Br | H | 50.22 | 3.07 | 5.32 | 50.16 | 3.02 | 5.33 | 191.5–192 |
| 44 | C₂₂H₁₅BrCl₂F₂N₂O₃ | F | F | H | CH₃ | Cl | CH₃ | Cl | H | Br | H | 48.56 | 2.78 | 5.15 | 48.86 | 2.91 | 4.96 | 199–200.5 |
| 45 | C₂₀H₉Cl₅F₂N₂O₃ | F | F | H | Cl | Cl | Cl | H | H | H | Cl | 44.44 | 1.68 | 5.18 | 43.92 | 1.67 | 5.10 | 212–213 |
| 46 | C₂₂H₁₅Cl₃F₂N₂O₃ | F | F | H | CH₃ | Cl | CH₃ | H | H | H | Cl | 52.88 | 3.03 | 5.61 | 53.97 | 3.58 | 5.26 | 201–203 |
| 47 | C₂₀H₁₀Cl₆N₂O₃ | Cl | Cl | H | Cl | Cl | Cl | H | H | H | Cl | 44.57 | 1.87 | 5.20 | 44.44 | 1.88 | 5.17 | 202–204 |
| 48 | C₂₂H₁₆Cl₄N₂O₃ | Cl | Cl | H | CH₃ | Cl | CH₃ | Cl | H | H | Cl | 53.05 | 3.24 | 5.62 | 53.16 | 3.46 | 5.53 | 185–186 |
| 49 | C₂₃H₁₈Cl₂F₂N₂O₃ | F | F | H | CH₃ | Cl | CH₃ | CH₃ | H | H | Cl | 57.62 | 3.79 | 5.84 | 57.36 | 3.75 | 5.92 | 201–203 |
| 50 | C₂₀H₈Br₁Cl₅F₂N₂O₃ | F | F | H | Br | Cl | Cl | Cl | H | H | Cl | 38.78 | 1.30 | 4.52 | 38.28 | 1.33 | 4.42 | 300–302 |
| 51 | C₂₂H₁₄Cl₄F₂N₂O₃ | F | F | H | CH₃ | Cl | CH₃ | Cl | H | H | Cl | 49.47 | 2.64 | 5.25 | 49.59 | 2.63 | 5.19 | 212–218 |
| 52 | C₂₀H₉Br₁Cl₆N₂O₃ | Cl | Cl | H | Br | Cl | Cl | Cl | H | H | Cl | 613.7928* | | | 613.7951* | | | 300–305 |
| 53 | C₂₂H₁₅Cl₅N₂O₃ | Cl | Cl | H | CH₃ | Cl | CH₃ | Cl | H | H | Cl | 49.60 | 2.84 | 5.26 | 49.06 | 2.92 | 5.15 | 224–228 |
| 54 | C₂₃H₁₈Cl₃F₁N₂O₃ | F | Cl | H | CH₃ | Cl | CH₃ | CH₃ | H | H | Cl | 55.72 | 3.66 | 5.65 | | | | 186–188 |
| 55 | C₂₃H₁₈Cl₃F₁N₂O₃ | Cl | F | H | CH₃ | Cl | CH₃ | CH₃ | H | H | Cl | 55.75 | 3.34 | 5.45 | | | | 208–210 |
| 56 | C₂₃H₁₈Cl₄N₂O₃ | Cl | Cl | H | CH₃ | Cl | CH₃ | CH₃ | H | H | Cl | 53.93 | 3.54 | 5.47 | | | | 185–187 |
| 57 | C₂₃H₁₇Cl₃F₂N₂O₃ | F | F | H | CH₃ | Cl | CH₃ | CH₃ | H | Cl | Cl | 53.77 | 3.34 | 5.45 | 54.81 | 3.54 | 5.12 | 191–193 |
| 58 | C₂₃H₁₈Cl₄N₂O₃ | F | Cl | H | CH₃ | Cl | CH₃ | CH₃ | H | H | Cl | 53.93 | 3.54 | 5.47 | 54.58 | 3.82 | 5.36 | 210–211 |
| 59 | C₂₃H₁₈Cl₃F₁N₂O₃ | F | Cl | H | CH₃ | Cl | CH₃ | CH₃ | H | H | Cl | 55.72 | 3.66 | 5.65 | 55.95 | 3.68 | 5.62 | 214–217 |
| 60 | C₂₄H₂₂Cl₂N₂O₃ | H | H | H | CH₃ | Cl | CH₃ | CH₃ | H | H | H | 63.03 | 4.85 | 6.12 | 63.33 | 4.94 | 6.09 | 165–166 |
| 61 | C₂₄H₂₁Cl₃N₂O₃ | Cl | H | H | CH₃ | Cl | CH₃ | CH₃ | H | H | H | 58.61 | 4.30 | 5.70 | 58.28 | 4.21 | 5.64 | 213–217 |
| 62 | C₂₄H₂₁Cl₂FN₂O₃ | F | H | H | CH₃ | Cl | CH₃ | CH₃ | H | H | H | 60.64 | 4.45 | 5.89 | 60.79 | 4.42 | 5.82 | 205–205.5 |
| 63 | C₂₃H₁₉BrCl₂N₂O₃ | Cl | H | H | CH₃ | Cl | CH₃ | Br | H | H | H | 62.82 | 4.61 | 6.10 | 62.94 | 4.88 | 6.03 | 183–185 |
| 64 | C₂₃H₁₈BrClF₂N₂O₃ | F | F | H | CH₃ | Cl | CH₃ | Br | H | H | H | 52.90 | 3.34 | 5.36 | 53.18 | 3.68 | 5.47 | 169–172 |
| 65 | C₂₃H₁₉BrClFN₂O₃ | F | H | H | CH₃ | Cl | CH₃ | Br | H | H | H | 49.62 | 3.67 | 5.03 | 49.60 | 3.29 | 4.99 | 223–224 |
| 66 | C₂₃H₁₈BrClF₂N₂O₃ | F | Cl | H | CH₃ | Cl | CH₃ | Br | H | H | H | 52.75 | 3.26 | 5.35 | 52.27 | 3.40 | 5.43 | 141–141.5 |
| 67 | C₂₃H₁₈BrCl₂N₂O₃ | Cl | Cl | H | CH₃ | Cl | CH₃ | Br | H | H | H | 52.92 | 3.67 | 5.36 | 52.43 | 3.68 | 5.31 | 171–173 |
| 68 | C₂₃H₁₈BrClF₂N₂O₃ | F | F | H | CH₃ | Cl | CH₃ | Br | H | H | H | 49.62 | 3.26 | 5.03 | 49.75 | 3.23 | 5.00 | 220–221 |
| 69 | C₂₃H₁₉Cl₃N₂O₃ | Cl | H | H | CH₃ | Cl | CH₃ | CH₃ | H | H | H | 52.75 | 3.46 | 5.35 | 52.97 | 3.49 | 5.31 | 174–176 |
| 70 | C₂₃H₁₈Cl₄N₂O₃ | Cl | Cl | H | CH₃ | Cl | CH₃ | CH₃ | H | H | H | 57.82 | 4.01 | 5.86 | 57.51 | 4.00 | 5.66 | 172–174.5 |
| 71 | C₂₃H₁₈Cl₂F₂N₂O₃ | F | F | H | CH₃ | Cl | CH₃ | CH₃ | H | H | H | 53.93 | 3.54 | 5.49 | 54.22 | 3.55 | 5.55 | 230–231 |
| 72 | C₂₃H₁₈Cl₃FN₂O₃ | F | Cl | H | CH₃ | Cl | CH₃ | CH₃ | H | H | H | 57.64 | 3.78 | 5.84 | 57.50 | 3.84 | 5.81 | 189–190 |
| 73 | C₂₃H₁₉Cl₃N₂O₃ | Cl | H | H | CH₃ | Cl | CH₃ | CH₃ | H | H | H | 57.82 | 4.01 | 5.86 | 58.20 | 4.17 | 5.72 | 192.5–193 |
| 74 | C₂₃H₁₈Cl₂F₂N₂O₃ | F | F | H | CH₃ | Cl | CH₃ | Cl | H | H | H | 53.93 | 3.54 | 5.49 | 53.91 | 3.51 | 5.50 | 216–217.5 |
| 75 | C₂₃H₁₈Cl₂F₂N₂O₃ | F | F | H | CH₃ | Cl | CH₃ | Cl | H | H | H | 57.64 | 3.78 | 5.84 | 57.82 | 3.84 | 5.73 | 177–179 |
| 76 | C₂₅H₂₄Cl₂N₂O₃ | H | H | H | CH₃ | Cl | CH₃ | CH₃ | CH₃ | CH₃ | H | 63.69 | 5.13 | 5.94 | 63.68 | 5.30 | 5.99 | 185–186 |
| 77 | C₂₅H₂₃Cl₃N₂O₃ | Cl | H | H | CH₃ | Cl | CH₃ | CH₃ | CH₃ | CH₃ | H | 59.36 | 4.58 | 5.54 | 59.52 | 4.82 | 5.47 | 205.5–207.5 |
| 78 | C₂₅H₂₃Cl₂FN₂O₃ | F | H | H | CH₃ | Cl | CH₃ | CH₃ | CH₃ | CH₃ | H | 61.35 | 4.74 | 5.72 | 61.49 | 4.81 | 5.77 | 204–205 |
| 79 | C₂₅H₂₃Cl₂FN₂O₃ | F | F | H | CH₃ | Cl | CH₃ | CH₃ | CH₃ | CH₃ | H | 63.49 | 4.90 | 5.92 | 63.58 | 5.20 | 5.92 | 217.5–218 |
| 80 | C₂₄H₁₂ClFN₂O₃ | F | H | H | CH₃ | Cl | CH₃ | CH₃ | H | CH₃ | H | 65.38 | 5.03 | 6.35 | 65.25 | 5.13 | 6.21 | 159–160 |

TABLE I-continued

Representative 1-(4-Phenoxyphenyl)-3-Benzoyl Urea Compounds

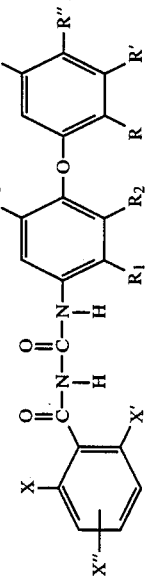

| Example | Molecular Formula | X | X' | X" | $R_1$ | $R_2$ | $R_3$ | R | R' | R" | R''' | Elemental Analysis Calculated C | H | N | Found C | H | N | Melting Point °C. |
|---|---|---|---|---|---|---|---|---|---|---|---|---|---|---|---|---|---|---|
| 81 | $C_{24}H_{22}ClFN_2O_3$ | F | H | H | $CH_3$ | Cl | $CH_3$ | $CH_3$ | H | H | $CH_3$ | 65.38 | 5.03 | 6.35 | 65.74 | 5.17 | 6.25 | 143.5–145.5 |
| 82 | $C_{24}H_{22}Cl_2N_2O_3$ | Cl | H | H | $CH_3$ | Cl | $CH_3$ | $CH_3$ | H | H | $CH_3$ | 63.03 | 4.85 | 6.12 | 63.14 | 5.13 | 6.06 | 174–176 |
| 83 | $C_{24}H_{21}ClF_2N_2O_3$ | F | F | H | $CH_3$ | Cl | $CH_3$ | $CH_3$ | H | H | $CH_3$ | 62.86 | 4.62 | 6.11 | 62.90 | 4.67 | 6.01 | 197–198 |
| 84 | $C_{24}H_{22}Cl_2N_2O_3$ | Cl | H | H | $CH_3$ | Cl | $CH_3$ | $CH_3$ | $CH_3$ | H | H | 63.03 | 4.85 | 6.12 | 63.35 | 5.39 | 6.36 | 193.5–194.5 |
| 85 | $C_{24}H_{21}Cl_2FN_2O_3$ | Cl | F | H | $CH_3$ | Cl | $CH_3$ | $CH_3$ | $CH_3$ | H | H | 60.64 | 4.45 | 5.89 | 61.29 | 4.46 | 5.78 | 193–195 |
| 86 | $C_{24}H_{21}ClF_2N_2O_3$ | F | F | H | $CH_3$ | Cl | $CH_3$ | $CH_3$ | $CH_3$ | H | H | 62.82 | 4.61 | 6.10 | 63.04 | 4.89 | 6.21 | 182.5–184 |
| 87 | $C_{24}H_{21}Cl_3N_2O_3$ | Cl | H | H | $CH_3$ | Cl | $CH_3$ | $CH_3$ | H | Cl | H | 58.61 | 4.30 | 5.70 | 58.87 | 4.53 | 5.70 | 204.5–206 |
| 88 | $C_{24}H_{20}Cl_3FN_2O_3$ | Cl | F | H | $CH_3$ | Cl | $CH_3$ | $CH_3$ | H | Cl | H | 56.54 | 3.95 | 5.50 | 57.41 | 4.27 | 5.57 | 217.5–219 |
| 89 | $C_{24}H_{20}Cl_2F_2N_2O_3$ | F | F | H | $CH_3$ | Cl | $CH_3$ | $CH_3$ | H | Cl | H | 58.43 | 4.09 | 5.68 | 58.59 | 4.27 | 5.65 | 201–202.5 |
| 90 | $C_{24}H_{21}Cl_3N_2O_3$ | F | H | H | $CH_3$ | Cl | $CH_3$ | $CH_3$ | H | Cl | $CH_3$ | 58.61 | 4.30 | 5.70 | 58.47 | 4.30 | 5.63 | 207–208 |
| 91 | $C_{24}H_{20}Cl_3FN_2O_3$ | Cl | F | H | $CH_3$ | Cl | $CH_3$ | $CH_3$ | H | Cl | $CH_3$ | 56.54 | 3.95 | 5.50 | 56.88 | 4.05 | 5.39 | 217–218 |
| 92 | $C_{24}H_{20}Cl_2N_2O_3$ | F | F | H | $CH_3$ | Cl | $CH_3$ | $CH_3$ | H | Cl | $CH_3$ | 58.43 | 4.09 | 5.68 | 58.72 | 4.18 | 5.68 | 221.5–222.5 |
| 93 | $C_{24}H_{21}BrCl_2N_2O_3$ | Cl | H | H | $CH_3$ | Cl | $CH_3$ | $CH_3$ | H | Br | H | 53.75 | 3.95 | 5.22 | 53.72 | 4.03 | 5.53 | 205–207 |
| 94 | $C_{24}H_{20}BrCl_2F_2N_2O_3$ | F | F | H | $CH_3$ | Cl | $CH_3$ | $CH_3$ | H | Br | H | 53.60 | 3.75 | 5.21 | 53.27 | 3.78 | 5.07 | 198–200 |
| 95 | $C_{25}H_{24}Cl_2N_2O_3$ | Cl | H | H | $CH_3$ | Cl | $CH_3$ | $CH_3$ | $CH_3$ | $CH_3$ | $CH_3$ | 63.70 | 5.13 | 5.94 | 63.64 | 5.24 | 6.03 | 175–181 |
| 96 | $C_{25}H_{23}ClF_2N_2O_3$ | F | F | H | $CH_3$ | Cl | $CH_3$ | $CH_3$ | $CH_3$ | $CH_3$ | $CH_3$ | 63.50 | 4.90 | 5.92 | 63.75 | 5.18 | 6.63 | 183.5–184.5 |
| 97 | $C_{24}H_{21}Cl_3N_2O_3$ | Cl | H | H | $CH_3$ | Cl | $CH_3$ | Cl | H | H | $CH_3$ | 58.61 | 4.30 | 5.70 | 59.19 | 4.68 | 5.60 | — |
| 98 | $C_{24}H_{20}Cl_2F_2N_2O_3$ | F | F | H | $CH_3$ | Cl | $CH_3$ | Cl | H | H | $CH_3$ | 58.43 | 4.09 | 5.68 | 58.64 | 4.36 | 5.64 | 197.5–200 |
| 99 | $C_{23}H_{18}Cl_4N_2O_4$ | Cl | H | H | $CH_3$ | Cl | $CH_3$ | Cl | H | Cl | $CH_3$ | 53.93 | 3.54 | 5.47 | 54.16 | 3.79 | 5.41 | 197–198.5 |
| 100 | $C_{23}H_{17}Cl_3F_2N_2O_3$ | F | F | H | $CH_3$ | Cl | $CH_3$ | Cl | H | Cl | $CH_3$ | 53.77 | 3.34 | 5.45 | 53.57 | 3.42 | 5.58 | 207–210 |
| 101 | $C_{24}H_{21}BrCl_2N_2O_3$ | Cl | H | H | $CH_3$ | Cl | $CH_3$ | $CH_3$ | H | Br | $CH_3$ | 53.75 | 3.76 | 5.22 | 53.96 | 4.04 | 5.20 | 213.5–215 |
| 102 | $C_{24}H_{20}BrClF_2N_2O_3$ | F | F | H | $CH_3$ | Cl | $CH_3$ | $CH_3$ | H | Br | $CH_3$ | 53.60 | 3.75 | 5.21 | 53.69 | 3.78 | 5.16 | 224–225.5 |

*Exact mass as determined by high resolution mass spectrometry.

Certain representative examples of the new compounds were evaluated to determine their pesticidal activity against certain insects, including a caterpillar and a beetle. The new compounds were also tested for phytotoxicity on important economic crops including snap bean, cucumber and sorghum. The new compounds were further evaluated for mammalian toxicity.

Suspensions of the test compounds were prepared by dissolving 100 milligrams of compound in 1.5 milliliters of dimethylforamide and then adding 8.5 milliliters of an acetone solution containing 0.25 percent of an alkylphenoxy polyethoxyethanol surfactant, as an emulsifying or dispersing agent. The resulting solution was mixed into 30 milliliters of water to give roughly 40 milliliters of a suspension containing the compound in finely divided form. The thus-prepared stock suspension contained 2.5 percent by weight of compound. The test concentrations in parts per million by weight employed in the tests described hereinbelow were obtained by appropriate dilutions of the stock suspension with water. Sonication was used where necessary to obtain a homogeneous suspension. The test procedures were as follows:

Southern Armyworm Leaf Spray Test

Larvae of the southern armyworm (*Spodoptera eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing the test compound at the concentrations (in parts of the test compound per million parts of final formulation) as set forth in the Tables below. Potted tendergreen bean plants of standard height and age were placed on a revolving turntable and sprayed with 100 milliliters of test compound formulation by use of a DeVilbiss spray gun set at 40 psig air pressure. This application, which lasted 25 seconds, was sufficient to wet plants to run-off. As a control, 100 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for five days. Although the larvae could easily consume the whole left within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Third instar larvae of the Mexican bean beetle (*Ephilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing the test compound at the concentrations (in parts of the test compound per million parts of final formulation) as set forth in the Tables below. Potted Tendergreen bean plants of standard height and age were placed on a revolving turntable and sprayed with 100 milliliters of test compound formulation by use of a DeVilbiss spray gun set at 40 psig air pressure. This application, which lasted 25 seconds, was sufficient to wet plants to run-off. As a control, 100 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead.

Tobacco Budworm and Cotton Bollworm Leaf Spray Bait Test

Second instar larvae of the tobacco budworm (weighing about 2.5 mg) (*Heliothis virescens*, F.) and the cotton bollworm (weighing about 2.5 mg) (*Heliothis zea*, (Boddie)), obtained commercially and reared on artificial diet at a temperature of 80°±5° and a relative humidity of 50±5 percent, constituted the test insects.

Using a procedure similar to the above, but substituting cotton plants for snapbeans, treated and dried cotton leaves were introduced into 9 cm Petri dishes which were organized in to groups of 10-dish sets. One randomly selected larvae was introduced into each dish of a ten dish set and the dishes were closed. The closed dishes were labelled and held at 80°±5° F. for five days. Larvae which were unable to move the length of the body, even upon stimulation, were considered dead. Percent mortality was recorded for various concentration levels.

The biological properties of certain representative examples of the compounds of this invention are set forth in Tables II, III, IV, V and VI below.

TABLE II

Biological Properties of Representative
1-(4-Phenoxyphenyl)-3-Benzoyl Urea Compounds

| Compound Prepared In Example No. | Activity at 100 ppm[3] | |
|---|---|---|
| | SAW[1] | MBB[2] |
| 1 | A* | A* |
| 2 | — | — |
| 3 | A* | A* |
| 4 | A | A |
| 5 | A° | A** |
| 6 | A° | A° |
| 7 | A | A |
| 8 | A | A |
| 9 | A | A |
| 10 | A* | A* |
| 11 | A* | A* |
| 12 | A* | A* |
| 13 | A* | A* |
| 14 | A | A |
| 15 | A* | A* |
| 16 | A | A |
| 17 | A | A |
| 18 | A | A |
| 19 | A | A |
| 20 | A | A |
| 21 | A* | A* |
| 22 | A | A |
| 23 | A | C |
| 24 | A* | A* |
| 25 | A | A |
| 26 | A | A |
| 27 | A | A |
| 28 | A | A |
| 29 | A | A |
| 30 | A | A |
| 31 | A | A |

TABLE II-continued
Biological Properties of Representative
1-(4-Phenoxyphenyl)-3-Benzoyl Urea Compounds

| Compound Prepared In Example No. | Activity at 100 ppm[3] SAW[1] | MBB[2] |
|---|---|---|
| 32 | A | A |
| 33 | A | A |
| 34 | A* | A* |
| 35 | A* | A* |
| 36 | A* | A* |
| 37 | A* | A* |
| 38 | A* | A* |
| 39 | A* | A* |
| 40 | A* | A* |
| 41 | A* | A* |
| 42 | A | A°° |
| 43 | A | A°° |
| 44 | A | A |
| 45 | A* | A* |
| 46 | A* | A* |
| 47 | A* | A* |
| 48 | A* | A* |
| 49 | A | A |
| 50 | A | A |
| 51 | A | A |
| 52 | A | C |
| 53 | A | A |
| 54 | A | A |
| 55 | A | A |
| 56 | A | A |
| 57 | A | A |
| 58 | A | A |
| 59 | A | A |
| 60 | A* | A* |
| 61 | A* | A* |
| 62 | A* | A* |
| 63 | A* | A* |
| 64 | A* | A* |
| 65 | A* | A* |
| 66 | A* | A* |
| 67 | A* | A* |
| 68 | A* | A* |
| 69 | A* | A* |
| 70 | A* | A* |
| 71 | A* | A* |
| 72 | A* | A* |
| 73 | A* | A* |
| 74 | A* | A* |
| 75 | A* | A* |
| 76 | A* | A* |
| 77 | A* | A* |
| 78 | A* | A* |
| 79 | A* | A* |
| 80 | A* | A* |
| 81 | A* | A* |
| 82 | A* | A* |
| 83 | A* | A* |
| 84 | A* | A* |
| 85 | A* | A* |
| 86 | A* | A* |
| 87 | A* | A* |
| 88 | A* | A* |
| 89 | A* | A* |
| 90 | A* | A* |
| 91 | A* | A* |
| 92 | A* | A* |
| 93 | A* | A* |
| 94 | A* | A* |
| 95 | A* | A* |
| 96 | A* | A* |
| 97 | A* | A* |
| 98 | A* | A* |
| 99 | A* | A* |
| 100 | A* | A* |
| 101 | A* | A* |
| 102 | A* | A* |

[1]Southern Armyworm
[2]Mexican Bean Beetle
[3]Code:
A = 71-100% Kill
B = 31-70% Kill
C = 0-30% Kill
*Tested at 500 ppm.
**Tested at 6.25 ppm.
°Tested at 25 ppm.
°°Tested at 8 ppm.

EXAMPLES 103 THROUGH 108 AND COMPARATIVE EXAMPLES A THROUGH D

In order to demonstrate the enhanced biological activity against Southern Armyworm and Mexican Bean Beetle, representative 1-(4phenoxyphenyl)-3-benzoyl urea compounds of this invention were compared with known compounds. The results are set forth in Table III below.

TABLE III
Comparison of Representative 1-(4-Phenoxyphenyl)-3-Benzoyl Urea Compounds with Known Coumpounds Against Southern Armyworm and Mexican Bean Beetle

| Example/ Comparative Example | Compound Structure | Southern Armyworm Application Rate (ppm) | Percent Control (after 5 days) | Mexican Bean Beetle Application Rate (ppm) | Percent Control (after 5 days) |
|---|---|---|---|---|---|
| A | (2-Cl-benzoyl)-NH-C(O)-NH-(4-(2,4-dichlorophenoxy)phenyl) | 0.4 | 0 | 6.25 | 20 |
| B | (2-Cl-benzoyl)-NH-C(O)-NH-(3-Cl-4-(2,4-dichlorophenoxy)phenyl) | 0.4 | 0 | 25 | 0 |

TABLE III-continued
Comparison of Representative 1-(4-Phenoxyphenyl)-3-Benzoyl Urea Compounds with Known Coumpounds Against Southern Armyworm and Mexican Bean Beetle

| Example/ Comparative Example | Compound Structure | Southern Armyworm | | Mexican Bean Beetle | |
|---|---|---|---|---|---|
| | | Application Rate (ppm) | Percent Control (after 5 days) | Application Rate (ppm) | Percent Control (after 5 days) |
| 103 | 2-Cl-benzoyl-NH-C(O)-NH-(2,3,5-trichloro-4-(2,4-dichlorophenoxy)phenyl) | 0.4 | 100 | 6.25 | 90 |
| 104 | 2-Cl-benzoyl-NH-C(O)-NH-(2,6-dimethyl-3-chloro-4-(2,4-dichlorophenoxy)phenyl) | 0.4 | 100 | 6.25 | 80 |
| 105 | 2-Cl-benzoyl-NH-C(O)-NH-(2,6-dimethyl-3-chloro-4-(2,4-dichlorophenoxy)phenyl) | 0.125 | 100 | 2 | 80 |
| C | 2,6-F-benzoyl-NH-C(O)-NH-(5-chloropyridin-2-yl-oxy-2,4-dichlorophenyl) | 0.4 | 30 | 25 | 0 |
| D | 2,6-F-benzoyl-NH-C(O)-NH-(3-methyl-4-(2,4-dichlorophenoxy)phenyl) | 0.4 | 50 | 6.25 | 30 |
| 106 | 2,6-F-benzoyl-NH-C(O)-NH-(2,6-dimethyl-3-chloro-4-(2-bromo-4-chlorophenoxy)phenyl) | 0.25 | 100 | 2 | 100 |
| 107 | 2,6-F-benzoyl-NH-C(O)-NH-(2-methyl-3,5-dichloro-4-(2,4-dichlorophenoxy)phenyl) | 0.4 | 100 | 1.6 | 100 |
| 108 | 2,6-F-benzoyl-NH-C(O)-NH-(2,6-dimethyl-3-chloro-4-(2,4-dichlorophenoxy)phenyl) | 0.125 | 100 | 0.62 | 100 |

From the data included in Table III, it is evident that the 1-(4-phenoxyphenyl)-3-benzoyl urea compounds of this invention provide significantly enhanced biological activity against the Southern Armyworm and Mexican Bean Beetle in comparison with known compounds. As used in Table III, the compound of Comparative Example A was prepared in a manner similar to the procedure described in U.S. Pat. No. 4,399,152. The compound of Comparative Example B was prepared in a manner similar to the procedure described in U.S. Pat. No. 4,068,002. The compound of Comparative Example C was prepared in a manner similar to the procedure described in European Patent Application Publication No. 0069288. The compound of Comparative Example D was prepared in a manner similar to the procedure described in Japanese Patent Application No. 55038 357.

EXAMPLE 109 THROUGH 114 AND COMPARATIVE EXAMLES E THROUGH H

In order to further demonstrate the enhanced biological activity against Mexican Bean Beetle, representative 1-(4-phenoxyphenyl)-3-benzoyl urea compounds of this invention were compared with known compounds. The results are set forth in Table IV below.

TABLE IV

Comparison of Representative 1-(4-Phenoxyphenyl)-3-Benzoyl Urea Compounds with Known Compounds Against Mexican Bean Beetle

| Example/ Comparative Example | Compound Structure | Mexican Bean Beetle Application Rate (ppm) | Percent Control (after 5 days) |
|---|---|---|---|
| E | [structure] | 4 | 40 |
| F | [structure] | 0.5 | 0 |
| G | [structure] | 0.5 | 0 |
| H | [structure] | 0.5 | 30 |
| 109 | [structure] | 0.4 | 100 |
| 110 | [structure] | 0.25 | 100 |
| 111 | [structure] | 0.5 | 100 |

TABLE IV-continued
Comparison of Representative 1-(4-Phenoxyphenyl)-3-Benzoyl Urea Compounds with Known Compounds Against Mexican Bean Beetle

| Example/Comparative Example | Compound Structure | Application Rate (ppm) | Percent Control (after 5 days) |
|---|---|---|---|
| 112 | [2-Cl-benzoyl]-NH-C(O)-NH-[3,5-di-CH$_3$-2-Cl-4-(4-F-phenoxy)phenyl] | 0.5 | 100 |
| 113 | [2-Cl-benzoyl]-NH-C(O)-NH-[3,5-di-CH$_3$-2-Cl-4-(2,5-di-Cl-phenoxy)phenyl] | 0.5 | 90 |
| 114 | [2,6-di-F-benzoyl]-NH-C(O)-NH-[3,5-di-CH$_3$-2-Cl-4-(2-CH$_3$-5-Cl-phenoxy)phenyl] | 0.4 | 100 |

From the data included in Table IV, it is evident that the 1-(4-phenoxyphenyl)-3-benzoyl urea compounds of this invention provide significantly enhanced biological activity against the Mexican Bean Beetle in comparison with known compounds. As used in Table IV, the compound of Comparative Example E was prepared in a manner similar to the procedure described in U.S. Pat. No. 4,399,152. The compound of Comparative Example F was prepared in a manner similar to the procedure described in U.S. Pat. No. 4,005,223. The compound of Comparative Example G was prepared in a manner similar to the procedure described in U.S. Pat. No. 4,005,223. The compound of Comparative Example H was prepared in a manner similar to the procedure described in U.S. Pat. No. 4,041,177.

EXAMPLES 115 THROUGH 121 AND COMPARATIVE EXAMPLES I THROUGH K

In order to further demonstrate the enhanced biological activity against Southern Armyworm, representative 1-(4-phenoxyphenyl)-3-benzoyl urea compounds of this invention were compared with known compounds. The results are set forth in Table V below.

TABLE V
Comparison of Representative 1-(4-Phenoxyphenyl)-3-Benzoyl Urea Compounds with Known Compounds Against Southern Armyworm

| Example/Comparative Example | Compound Structure | Application Rate (ppm) | Percent Control (after 5 days) |
|---|---|---|---|
| I | [2,6-di-F-benzoyl]-NH-C(O)-NH-[3-CH$_3$-4-(2-Cl-4-NO$_2$-phenoxy)phenyl] | 0.125 | 0 |
| J | [2,6-di-F-benzoyl]-NH-C(O)-NH-[3,5-di-Cl-4-(4-NO$_2$-phenoxy)phenyl] | 0.125 | 10 |
| K | [2,6-di-F-benzoyl]-NH-C(O)-NH-[3,5-di-CH$_3$-2-Cl-4-(2-CH$_3$-5-CF$_3$-phenoxy)phenyl] | 0.1 | 10 |

TABLE V-continued
Comparison of Representative 1-(4-Phenoxyphenyl)-3-Benzoyl Urea Compounds with Known Compounds Against Southern Armyworm

| Example/Comparative Example | Compound Structure | Southern Armyworm Application Rate (ppm) | Percent Control (after 5 days) |
| --- | --- | --- | --- |
| 115 | [2,6-difluorobenzoyl urea with 3,5-dimethyl-4-(2,4-dichlorophenoxy)phenyl, additional CH₃] | 0.1 | 90 |
| 116 | [2,6-difluorobenzoyl urea with 3,5-dichloro-2-methyl-4-(2,4-dichlorophenoxy)phenyl] | 0.1 | 100 |
| 117 | [2-fluorobenzoyl urea with 2-methyl-3,5-dichloro-4-(2,4-dichlorophenoxy)phenyl] | 0.125 | 100 |
| 118 | [2-chlorobenzoyl urea with 2-methyl-3-chloro-5-bromo-4-(2-chloro-4-chlorophenoxy)phenyl with CH₃] | 0.1 | 100 |
| 119 | [2-fluorobenzoyl urea with 2-methyl-3-chloro-5-methyl-4-(2-bromo-4-chlorophenoxy)phenyl] | 0.1 | 100 |
| 120 | [2-fluorobenzoyl urea with 2-methyl-3-methyl-5-chloro-4-(2-bromo-4-chlorophenoxy)phenyl] | 0.1 | 100 |
| 121 | [2,6-difluorobenzoyl urea with 2-methyl-3,5-dichloro-4-(2-chloro-4-fluorophenoxy)phenyl] | 0.125 | 100 |

From the data included in Table V, it is evident that the 1-(4-phenoxyphenyl)-3-benzoyl urea compounds of this invention provide significantly enhanced biological activity against the Southern Armyworm in comparison with known compounds. As used in Table V, the compound of Comparative Example I was prepared in a manner similar to the procedure described in U.S. Pat. No. 4,005,223. The compound of Comparative Example J was prepared in a manner similar to the procedure described in U.S. Pat. No. 4,041,177. The compound of Comparative Example K was prepared in a manner similar to the procedure described in Japanese patent application No. 56 092 857.

EXAMPLES 122 THROUGH 124 AND COMPARATIVE EXAMPLES L AND M

In order to demonstrate the enhanced biological activity against *Heliothis* ssp., representative 1-(4-phenoxyphenyl)-3-benzoyl urea compounds of this invention were compared with known compounds. The results are set forth in Table VI below.

TABLE VI

Comparison of Representative 1-(4-Phenoxyphenyl)-3-Benzoyl Urea Compounds with Known Compounds Against Heliothis

| Example/ Comparative Example | Compound Structure | *Heliothis Zea* | | *Heliothis Virescens* | |
|---|---|---|---|---|---|
| | | Application Rate (ppm) | Percent Control (after 5 days) | Application Rate (ppm) | Percent Control (after 5 days) |
| L | (structure) | 2 | 20 | 8 | 0 |
| M | (structure) | 0.5 | 10 | 0.5 | 0 |
| 122 | (structure) | 0.5 | 80 | 0.5 | 80 |
| 123 | (structure) | 0.5 | 100 | 0.5 | 100 |
| 124 | (structure) | 0.5 | 90 | 0.5 | 60 |

From the data included in Table VI, it is evident that the 1-(4-phenoxyphenyl)-3-benzoyl urea compounds of this invention provide significantly enhanced biological activity against *Heliothis* spp. in comparison with known compounds. As used in Table VI, the compound of Comparative Example L was prepared in a manner similar to the procedure described in U.S. Pat. No. 4,005,223. The compound of Comparative Example M was prepared in a manner similar to the procedure described in U.S. Pat. No. 4,005,223.

Although the invention has been illustrated by the foregoing examples, it is not to be construed as being limited to the materials employed therein; but rather, the invention encompasses the generic area as hereinabove disclosed. Various modifications and embodiments can be made without departing from the spirit and scope thereof.

We claim:

1. A compound of the formula:

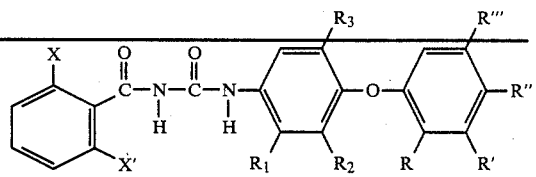

wherein:
X represents halogen;
X' represents hydrogen or halogen;
$R_1$, $R_2$ and $R_3$ are independently methyl, chlorine or bromine;
R represents methyl, chlorine, fluorine or bromine; and
R', R" and R''' are independently hydrogen, methyl, chlorine, fluorine or bromine, provided that at least one of R', R", and R''' is other than hydrogen.

2. The compound of claim 1 wherein X' represent hydrogen.

3. The compound of claim 1 which has the formula:

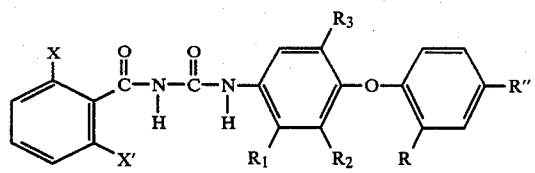

wherein X, X', $R_1$, $R_2$ $R_3$, R and R" are as indicated in claim 1.

4. The compound of claim 1 which has the formula:

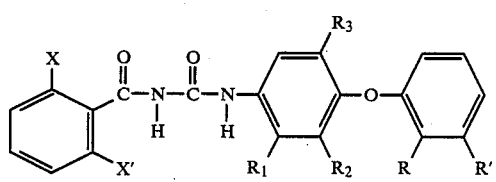

wherein X, X', $R_1$, $R_2$, $R_3$, R and R' are as indicated in claim 1.

5. The compound of claim 1 which has the formula:

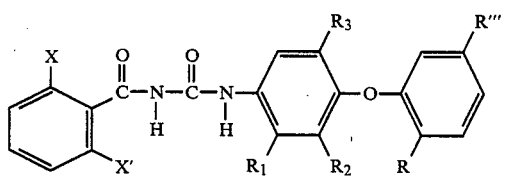

wherein X, X', $R_1$, $R_2$, $R_3$, R and R''' are as indicated in claim 1.

6. The compound of claim 1 which has the formula:

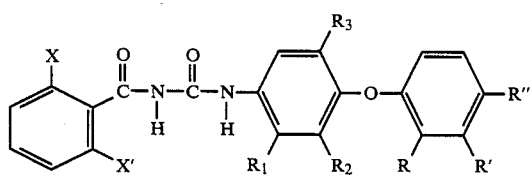

wherein X, X', $R_1$, $R_2$, $R_3$, R, R' and R" are as indicated in claim 1.

7. The compound of claim 1 which has the formula:

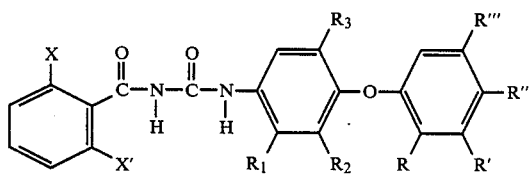

wherein X, X', $R_1$, $R_2$, $R_3$, R, R' and R''' are as indicated in claim 1.

8. The compound of claim 1 which has the formula:

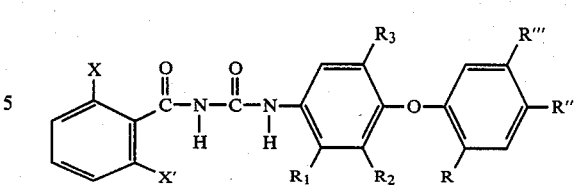

wherein X, X', $R_1$, $R_2$, $R_3$, R, R" and R''' are as indicated in claim 1.

9. The compound of claim 1 which has the formula:

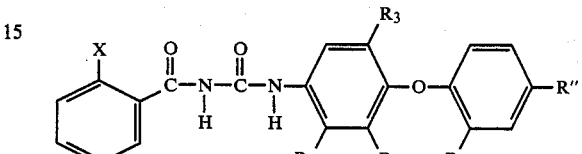

wherein X, $R_1$, $R_2$, $R_3$, R and R" are as indicated in claim 1.

10. The compound of claim 1 which has the formula:

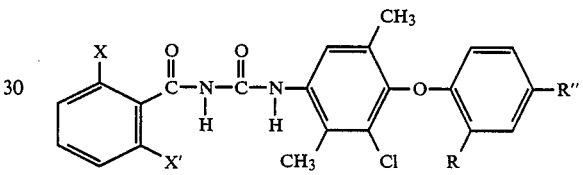

wherein X, X', R and R" are as indicated in claim 1.

11. The compound of claim 1 which has the formula:

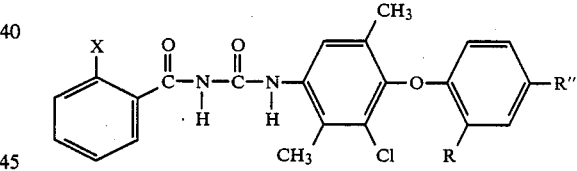

wherein X, R and R" are as indicated in claim 1.

12. The compound of claim 3 wherein X' is halogen and R and R" are independently methyl, bromine or chlorine.

13. The compound of claim 3 wherein X' is hydrogen and R and R" are independently methyl, bromine or chlorine.

14. The compound of claim 3 wherein X and X' are fluorine and R and R" are independently methyl, bromine or chlorine.

15. The compound of claim 5 wherein R and R''' are independently methyl, bromine or chlorine.

16. The compound of claim 6 wherein R, R' and R" are independently methyl, bromine or chlorine.

17. The compound of claim 8 wherein R, R" and R''' are independently methyl, bromine or chlorine.

18. The compound of claim 9 wherein X is fluorine and R and R" are independently methyl, bromine or chlorine.

19. The compound of claim 10 wherein X and X' are fluorine and R and R" are independently methyl, bromine or chlorine.

20. The compound of claim 10 wherein X and X' are fluorine, R is chlorine or bromine and R" is chlorine.

21. The compound of claim 11 wherein X is fluorine and R and R" are independently methyl, bromine or chlorine.

22. The compound of claim 11 wherein X is fluorine, R is chlorine or bromine and R" is chlorine.

23. The compound of claim 1 which is 1-[3-chloro-4-(2,4-dichlorophenoxy)-2,5-dimethylphenyl]-3-(2,6-difluorobenzoyl)urea.

24. The compound of claim 1 which is 1-[3-chloro-4-(2-bromo-4-chlorophenoxy)-2,5-dimethylphenyl]-3-(2,6-difluorobenzoyl)urea.

25. The compound of claim 1 which is 1-[3-chloro-4-(2-bromo-4-chlorophenoxy)-2,5-dimethylphenyl]-3-(2-fluorobenzoyl)urea.

26. The compound of claim 1 which is 1-[3-chloro-4-(2,4-dichlorophenoxy)-2,5-dimethylphenyl]-3-(2-chlorobenzoyl)urea.

27. The compound of claim 1 which is 1-[3-chloro-4-(2,4-dichlorophenoxy)-2,5-dimethylphenyl]-3-(2-fluorobenzoyl)urea.

28. The compound of claim 1 which is 1-[3-chloro-4-(2,4-dibromophenoxy)-2,5-dimethylphenyl]-3-(2,6-difluorobenzoyl)urea.

29. The compound of claim 1 which is 1-[3-chloro-4-(2,4-dibromophenoxy-2,5-dimethylphenyl]-3-(2-fluorobenzoyl)urea.

30. The compound of claim 1 which is 1-[4-(2,4-dichlorophenoxy)-2,3,5-trimethylphenyl]-3-(2,6-difluorobenzoyl)urea.

31. The compound of claim 1 which is 1-[4-(2,4-dichlorophenoxy)-2,3,5-trichlorophenyl]-3-(2,6-difluorobenzoyl)urea.

32. The compound of claim 1 which is 1-[2,3-dichloro-4-(2,4-dichlorophenoxy)-5-methylphenyl]-3-(2,6-difluorobenzoyl)urea.

33. The compound of claim 1 which is 1-[2-chloro-4-(2,4-dichlorophenoxy)-3,5-dimethylphenyl]-3-(2,6-difluorobenzoyl)urea.

34. The compound of claim 1 which is 1-[4-(2-bromo-4-chlorophenoxy)-2,3,5-trimethylphenyl]-3-(2,6-difluorobenzoyl)urea.

35. The compound of claim 1 which is 1-[4-(2-bromo-4-chlorophenoxy)-2-chloro-3,5-dimethylphenyl]-3-(2,6-difluorobenzoyl)urea.

36. The compound of claim 1 which is 1-[4-(2-bromo-4-chlorophenoxy)-2-chloro-3,5-dimethylphenyl]-3-(2-fluorobenzoyl)urea.

37. An insecticide composition comprising an acceptable carrier and an insecticidally effective amount of the compound of claim 1.

38. An insecticide composition comprising an acceptable carrier and an insecticidally effective amount of the compound of claim 2.

39. An insecticide composition comprising an acceptable carrier and an insecticidally effective amount of the compound of claim 3.

40. An insecticide composition comprising an acceptable carrier and an insecticidally effective amount of the compound of claim 4.

41. An insecticide composition comprising an acceptable carrier and an insecticidally effective amount of the compound of claim 5.

42. An insecticide composition comprising an acceptable carrier and an insecticidally effective amount of the compound of claim 6.

43. An insecticide composition comprising an acceptable carrier and an insecticidally effective amount of the compound of claim 7.

44. An insecticide composition comprising an acceptable carrier and an insecticidally effective amount of the compound of claim 8.

45. An insecticide composition comprising an acceptable carrier and an insecticidally effective amount of the compound of claim 9.

46. An insecticide composition comprising an acceptable carrier and an insecticidally effective amount of the compound of claim 10.

47. An insecticide composition comprising an acceptable carrier and an insecticidally effective amount of the compound of claim 11.

48. An insecticide composition comprising an acceptable carrier and an insecticidally effective amount of the compound of claim 23.

49. An insecticide composition comprising an acceptable carrier and an insecticidally effective amount of the compound of claim 24.

50. An insecticide composition comprising an acceptable carrier and an insecticidally effective amount of the compound of claim 25.

51. A method of controlling insects which comprises subjecting said insects to an insecticidally effective amount of the composition of claim 1.

52. A method of controlling insects which comprises subjecting said insects to an insecticidally effective amount of the composition of claim 2.

53. A method of controlling insects which comprises subjecting said insects to an insecticidally effective amount of the composition of claim 3.

54. A method of controlling insects which comprises subjecting said insects to an insecticidally effective amount of the composition of claim 4.

55. A method of controlling insects which comprises subjecting said insects to an insecticidally effective amount of the compositions of claim 5.

56. A method of controlling insects which comprises subjecting said insects to an insecticidally effective amount of the composition of claim 6.

57. A method of controlling insects which comprises subjecting said insects to a an insecticidally effective amount of the composition of claim 7.

58. A method of controlling insects which comprises subjecting said insects to an insecticidally effective amount of the composition of claim 8.

59. A method of controlling insects which comprises subjecting said insects to an insecticidally effective amount of the composition of claim 9.

60. A method of controlling insects which comprises subjecting said insects to an insecticidally effective amount of the composition of claim 10.

61. A method of controlling insects which comprises subjecting said insects to an insecticidally effective amount of the composition of claim 11.

62. A method of controlling insects which comprises subjecting said insects to an insecticidally effective amount of the composition of claim 23.

63. A method of controlling insects which comprises subjecting said insects to an insecticidally effective amount of the composition of claim 24.

64. A method of controlling insects which comprises subjecting said insects to an insecticidally effective amount of the composition of claim 25.

* * * * *